(12) United States Patent
Gao et al.

(10) Patent No.: US 8,178,563 B2
(45) Date of Patent: May 15, 2012

(54) COMPOUNDS AND COMPOSITIONS AS HEDGEHOG PATHWAY MODULATORS

(75) Inventors: Wenqi Gao, San Diego, CA (US);
Jiqing Jiang, San Diego, CA (US);
Yongqin Wan, Irvine, CA (US); Dai Cheng, San Diego, CA (US); Dong Han, San Diego, CA (US); Xu Wu, San Diego, CA (US); Shifeng Pan, San Diego, CA (US)

(73) Assignee: IRM LLC, Hamilton (BM)

( * ) Notice: Subject to any disclaimer, the term of this patent is extended or adjusted under 35 U.S.C. 154(b) by 644 days.

(21) Appl. No.: 12/299,290

(22) PCT Filed: May 4, 2007

(86) PCT No.: PCT/US2007/068292
§ 371 (c)(1),
(2), (4) Date: Jan. 29, 2009

(87) PCT Pub. No.: WO2007/131201
PCT Pub. Date: Nov. 15, 2007

(65) Prior Publication Data
US 2009/0203666 A1 Aug. 13, 2009

Related U.S. Application Data

(60) Provisional application No. 60/797,949, filed on May 5, 2006.

(51) Int. Cl.
*A61K 31/44* (2006.01)
*C07D 213/72* (2006.01)

(52) U.S. Cl. .......................... 514/352; 546/304

(58) Field of Classification Search .................. None
See application file for complete search history.

(56) References Cited

U.S. PATENT DOCUMENTS

| | | | |
|---|---|---|---|
| 7,056,942 B2 * | 6/2006 | Hildesheim et al. | 514/411 |
| 2001/0020030 A1 | 9/2001 | Stewart et al. | |
| 2003/0139427 A1 | 7/2003 | Castelhano et al. | |
| 2006/0270686 A1 | 11/2006 | Kelly et al. | |
| 2006/0281791 A1 | 12/2006 | Keating et al. | |
| 2007/0161582 A1 | 7/2007 | Mijikovic et al. | |
| 2007/0275984 A1 | 11/2007 | Imogai et al. | |
| 2008/0280891 A1 | 11/2008 | Kelly et al. | |

FOREIGN PATENT DOCUMENTS

| | | |
|---|---|---|
| RU | 2179969 C2 | 9/2001 |
| WO | WO 97/20842 A1 | 6/1997 |
| WO | WO 99/18096 A1 | 4/1999 |
| WO | WO 01/44172 A1 | 6/2001 |
| WO | WO 01/44260 A2 | 6/2001 |
| WO | WO 01/49688 A1 | 7/2001 |
| WO | WO 02/22597 A1 | 3/2002 |
| WO | WO 03/015774 A1 | 2/2003 |
| WO | W02004/002948 A1 | 1/2004 |
| WO | WO 2004/004720 A1 | 1/2004 |
| WO | WO 2004/050643 A2 | 6/2004 |
| WO | WO 2004/072025 A2 | 8/2004 |
| WO | WO 2005/000309 A2 | 1/2005 |
| WO | WO 2005/014533 A2 | 2/2005 |
| WO | WO 2005/023761 A2 | 3/2005 |
| WO | W02005/030206 A1 | 4/2005 |
| WO | W02005/033288 A2 | 4/2005 |
| WO | WO 2005/044007 A1 | 5/2005 |
| WO | WO 2005/063258 A1 | 7/2005 |
| WO | W02006/028958 A2 | 3/2006 |
| WO | WO 2006/022955 A2 | 3/2006 |
| WO | W02006/039718 A2 | 4/2006 |
| WO | W02006/044975 A2 | 4/2006 |
| WO | WO 2006/042949 A1 | 4/2006 |
| WO | WO 2006/052936 A2 | 5/2006 |
| WO | W02006/078283 A2 | 7/2006 |
| WO | WO 2006/080884 A1 | 8/2006 |
| WO | WO 2006/122926 A1 | 11/2006 |
| WO | WO 2007/008627 A2 | 1/2007 |
| WO | W02007/031791 A1 | 3/2007 |
| WO | WO 2008/008059 A1 | 1/2008 |
| WO | WO 2008/014291 A2 | 1/2008 |
| WO | WO 2008/051502 A1 | 5/2008 |
| WO | WO 2008/077631 A1 | 7/2008 |
| WO | WO 2008/154259 A1 | 12/2008 |
| WO | WO 2009/009041 A2 | 1/2009 |
| WO | WO 2009/075874 A1 | 6/2009 |
| WO | WO 2009/078992 A1 | 6/2009 |

OTHER PUBLICATIONS

Rubin. Nature Reviews: Drug Discovery, 2006, 5, 1026-1033.*
Xu, et al., "N'(4-{[4-(1H-Benzoimidazol-2-yl)-arylamino]-methyl}-phenyl)-benzamide derivatives as small molecule heparanase inhibitors", Bioorganic & medicinal Chemistry Letters, 2006, pp. 404-408, vol. 16, Elsevier Ltd.

* cited by examiner

*Primary Examiner* — Noble Jarrell
(74) *Attorney, Agent, or Firm* — Chihang Amy Smith; Genomics Institute of the Novartis Research Foundation

(57) ABSTRACT

The invention provides a method for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula I.

12 Claims, No Drawings

COMPOUNDS AND COMPOSITIONS AS HEDGEHOG PATHWAY MODULATORS

CROSS-REFERENCE TO RELATED APPLICATIONS

This application is a 371 U.S. national phase application of international application number PCT/US2007/068292 filed 04 May 2007, which application claims priority to U.S. provisional patent application No. 60/797,949, filed 05 May 2006. The full disclosure of these applications is incorporated herein by reference in its entirety and for all purposes.

BACKGROUND

1. Field of the Invention

The invention provides a method for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula I.

2. Background of the Invention

During embryonic development, the hedgehog signaling pathway is essential for numerous processes such as the control of cell proliferation, differentiation and tissue patterning. The aberrant activity of the hedgehog signaling pathway, for example, as a result of enhanced activation, however may have pathological consequences. In this regard, activation of the hedgehog pathway in adult tissues can result in specific types of cancer that include, but are not limited to, cancers of the brain, muscle and skin, prostrate, medulloblastoma, pancreatic adenocarcinomas and small-cell lung carcinomas. Enhanced activation of the hedgehog signaling pathway contributes to the pathology and/or symptomology of a number of diseases. Accordingly, molecules that modulate the activity of the hedgehog signaling pathway are useful as therapeutic agents in the treatment of such diseases.

SUMMARY OF THE INVENTION

In one aspect, the present invention provides compounds of Formula I:

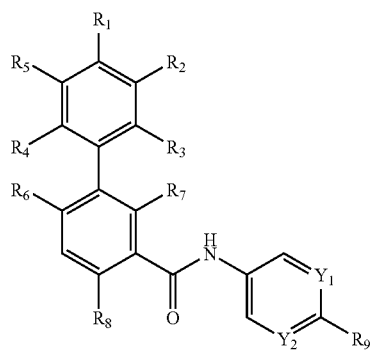

I in which $Y_1$ and $Y_2$ are independently selected from N and $CR_{10}$; wherein $R_{10}$ is selected from hydrogen, halo, $C_{1-6}$alkyl, halo-substituted-$C_{1-6}$alkyl, $C_{1-6}$alkoxy, halosubstituted-$C_{1-6}$alkoxy and —$OXNR_{10a}R_{10b}$; wherein $R_{10a}$ and $R_{10b}$ are independently selected from hydrogen and $C_{1-6}$alkyl;

$R_1$ is selected from cyano, halo, $C_{1-6}$alkyl, halosubstituted-$C_{1-6}$alkyl, $C_{1-6}$alkoxy, halosubstituted-$C_{1-6}$alkoxy, $C_{6-10}$aryl, dimethyl-amino, $C_{1-6}$alkyl-sulfanyl and $C_{3-8}$heterocycloalkyl optionally substituted with up to 2 $C_{1-6}$alkyl radicals;

$R_2$ and $R_5$ are independently selected from hydrogen, cyano, halo, $C_{1-6}$alkyl, halosubstituted-$C_{1-6}$alkyl, $C_{1-6}$alkoxy, halosubstituted-$C_{1-6}$alkoxy and dimethylamino;

$R_3$ and $R_4$ are independently selected from hydrogen, halo, cyano, $C_{1-6}$alkyl, halosubstituted-$C_{1-6}$alkyl, $C_{1-6}$alkoxy and halosubstituted-$C_{1-6}$alkoxy; or either $R_1$ and $R_2$ or $R_1$ and $R_5$ together with the phenyl to which they are both attached form $C_{5-10}$heteroaryl;

$R_6$ and $R_7$ are independently selected from hydrogen, $C_{1-6}$alkyl, halosubstituted-$C_{1-6}$alkyl, $C_{1-6}$alkoxy and halosubstituted-$C_{1-6}$alkoxy; with the proviso that $R_6$ and $R_7$ are not both hydrogen;

$R_8$ is selected from hydrogen, halo, $C_{1-6}$alkyl, halosubstituted-$C_{1-6}$alkyl, $C_{1-6}$alkoxy and halosubstituted-$C_{1-6}$alkoxy;

$R_9$ is selected from —$S(O)_2R_{11}$, —$C(O)R_{11}$, —$OR_{11}$, —$NR_{12a}R_{12b}$ and —$R_{11}$; wherein $R_{11}$ is selected from aryl, heteroaryl, cycloalkyl and heterocycloalkyl; $R_{12a}$ and $R_{12b}$ are independently selected from $C_{1-6}$alkyl and hydroxy-substituted-$C_{1-6}$alkyl;

wherein said aryl, heteroaryl, cycloalkyl and heterocycloalkyl of $R_9$ can be optionally substituted with 1 to 3 radicals independently selected from $C_{1-6}$alkyl, halosubstituted-$C_{1-6}$alkyl, $C_{1-6}$alkoxy, halosubstituted-$C_{1-6}$alkoxy, $C_{6-10}$aryl-$C_{0-4}$alkyl, $C_{5-10}$heteroaryl-$C_{0-4}$alkyl, $C_{3-12}$cycloalkyl and $C_{3-8}$heterocycloalkyl;

wherein said aryl-alkyl substituent of $R_9$ is optionally substituted with 1 to 3 radicals independently selected from halo, $C_{1-6}$alkyl, halosubstituted-$C_{1-6}$alkyl, $C_{1-6}$alkoxy, halosubstituted-$C_{1-6}$alkoxy and methyl-piperazinyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of the hedgehog pathway activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which hedgehog pathway activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

"Hedgehog gain-of-function" refers to an aberrant modification or mutation of a Ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the Ptc gene product to regulate the level of expression of Gli genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

"Patched loss-of-function" refers to an aberrant modification or mutation of a Ptc gene, or a decreased level of expression of the gene, which results in a phenotype which resembles contacting a cell with a hedgehog protein, e.g., aberrant activation of a hedgehog pathway. The loss-of-function may include a loss of the ability of the Ptc gene product to regulate the level of expression of Gli genes, e.g., Gli1, Gli2 and Gli3.

"Gli gain-of-function" refers to an aberrant modification or mutation of a Gli gene, or an increased level of expression of the gene, which results in a phenotype which resembles contacting a cell with a hedgehog protein, e.g., aberrant activation of a hedgehog pathway.

"Smoothened gain-of-function" refers to an aberrant modification or mutation of a Smo gene, or an increased level of expression of the gene, which results in a phenotype which resembles contacting a cell with a hedgehog protein, e.g., aberrant activation of a hedgehog pathway.

"Treat", "treating" and "treatment" refer to a method of alleviating or abating a disease and/or its attendant symptoms.

The present invention relates to the discovery that signal transduction pathways regulated by hedgehog, patched (Ptc), gli and/or smoothened can be modulated by compounds of Formula I.

DESCRIPTION OF PREFERRED EMBODIMENTS

In one embodiment, with respect to compounds of Formula I, $Y_1$ and $Y_2$ are selected from N and $CR_{10}$; wherein $R_{10}$ is selected from hydrogen, methyl, fluoro, chloro, bromo, dimethylamino-ethoxy and trifluoromethyl; $R_6$ and $R_7$ are independently selected from hydrogen methyl, chloro, fluoro, bromo, trifluoromethyl and methoxy; with the proviso that $R_6$ and $R_7$ are not both hydrogen; and $R_8$ is selected from hydrogen, fluoro, chloro, methyl and trifluoromethyl.

In another embodiment, $R_1$ is selected from cyano, chloro, fluoro, methyl, ethyl, t-butyl, propyl, isobutyl, isopropyl, isopropyloxy, butoxy, methoxy, dimethyl-amino, ethoxy, methyl-sulfanyl, phenyl, trifluoromethyl, trifluoromethoxy and piperazinyl optionally substituted with up to 2 methyl radicals; $R_2$ and $R_5$ are independently selected from hydrogen, chloro, fluoro, cyano, methyl, trifluoromethyl, isopropyloxy, methoxy, ethoxy, trifluoromethoxy and dimethylamino; and $R_3$ and $R_4$ are independently selected from hydrogen, chloro, methyl, methoxy and cyano; or either $R_1$ and $R_2$ or $R_1$ and $R_5$ together with the phenyl to which they are both attached form quinoxalinyl.

In another embodiment, $R_9$ is selected from —S(O)$_2$R$_{11}$, —OR$_{11}$, —C(O)R$_{11}$, —NR$_{12a}$R$_{12b}$ and —R$_{11}$; wherein $R_{11}$ is selected from thiomorpholino, sulfonomorpholino, sulfanomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl and 1,4-diazepan-1-yl; $R_{12a}$ and $R_{12b}$ are independently selected from isobutyl and hydroxy-ethyl; wherein said thiomorpholino, sulfonomorpholino, sulfanomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl or 1,4-diazepan-1-yl of $R_9$ can be optionally substituted with 1 to 3 radicals independently selected from methyl, ethyl, methoxy, benzyl, thienyl-methyl, pyridinyl-methyl, benzo[d][1,3]dioxol-6-yl and 2,3-dihydrobenzo[b][1,4]dioxin-7-yl; wherein said phenyl or benzyl substituent of $R_9$ is optionally substituted with 1 to 3 radicals independently selected from methoxy, ethoxy, methyl-piperazinyl, methyl, trifluoromethoxy, chloro, fluoro and trifluoromethyl.

Preferred compounds of Formula I are selected from 4'-cyano-6-methyl-biphenyl-3-carboxylic acid [4-(morpholine-4-sulfonyl)-phenyl]-amide, 4'-cyano-6-methyl-biphenyl-3-carboxylic acid [6-(2,6-dimethyl-morpholin-4-yl)-pyridin-3-yl]-amide, 4'-Cyano-2-methyl-biphenyl-3-carboxylic acid (6-azepan-1-yl-pyridin-3-yl)-amide, 4'-Methoxy-2-methyl-biphenyl-3-carboxylic acid (6-azepan-1-yl-pyridin-3-yl)-amide, 4'-Methoxy-2-methyl-biphenyl-3-carboxylic acid (4-cyclohexyl-phenyl)-amide, 4'-Methoxy-2-methyl-biphenyl-3-carboxylic acid [6-(2-methyl-morpholin-4-yl)-pyridin-3-yl]-amide, 4'-Dimethylamino-2-methyl-biphenyl-3-carboxylic acid (4-cyclohexyl-phenyl)-amide, 4'-Dimethylamino-2-methyl-biphenyl-3-carboxylic acid (4-morpholin-4-yl-phenyl)-amide, 6-Chloro-4'-dimethylamino-biphenyl-3-carboxylic acid (6-[1,4]oxazepan-4-yl-pyridin-3-yl)-amide, 6-Chloro-4'-dimethylamino-biphenyl- 3-carboxylic acid (6-morpholin-4-yl-pyridin-3-yl)-amide, 6-Chloro-4'-dimethylamino-biphenyl-3-carboxylic acid (6-azepan-1-yl-pyridin-3-yl)-amide, 6-Chloro-4'-methoxy-biphenyl-3-carboxylic acid [6-(2-methyl-morpholin-4-yl)-pyridin-3-yl]-amide, 6-Chloro-4'-methoxy-biphenyl-3-carboxylic acid (6-[1,4]oxazepan-4-yl-pyridin-3-yl)-amide, 6-Chloro-4'-methoxy-biphenyl-3-carboxylic acid (6-azepan-1-yl-pyridin-3-yl)-amide, 6-Chloro-4'-methoxy-biphenyl-3-carboxylic acid (6-morpholin-4-yl-pyridin-3-yl)-amide, 4'-Methoxy-6-methyl-biphenyl-3-carboxylic acid (6-morpholin-4-yl-pyridin-3-yl)-amide, 4'-Methoxy-6-methyl-biphenyl-3-carboxylic acid (6-[1,4]oxazepan-4-yl-pyridin-3-yl)-amide, 4'-Methoxy-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid (6-[1,4]oxazepan-4-yl-pyridin-3-yl)-amide, 4'-Dimethylamino-6-methyl-biphenyl-3-carboxylic acid (6-morpholin-4-yl-pyridin-3-yl)-amide, 4'-Methoxy-6-methyl-biphenyl-3-carboxylic acid (6-azepan-1-yl-pyridin-3-yl)-amide, 4'-Ethoxy-6-methyl-biphenyl-3-carboxylic acid (6-azepan-1-yl-pyridin-3-yl)-amide, 6-Methyl-4'-methylsulfanyl-biphenyl-3-carboxylic acid (6-azepan-1-yl-pyridin-3-yl)-amide, 4'-Dimethylamino-6-methyl-biphenyl-3-carboxylic acid (6-azepan-1-yl-pyridin-3-yl)-amide, 6-Methyl-[1,1';4',1"]terphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 2',4'-Dichloro-6-methyl-biphenyl-3-carboxylic acid (6-azepan-1-yl-pyridin-3-yl)-amide, 2'-Chloro-6-methyl-biphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 3',4'-Dichloro-6-methyl-biphenyl-3-carboxylic acid (6-azepan-1-yl-pyridin-3-yl)-amide, 3'-Chloro-6-methyl-4'-trifluoromethyl-biphenyl-3-carboxylic acid (6-azepan-1-yl-pyridin-3-yl)-amide, 6,4'-Dimethyl-biphenyl-3-carboxylic acid (6-azepan-1-yl-pyridin-3-yl)-amide, 4'-Ethyl-6-methyl-biphenyl-3-carboxylic acid (6-azepan-1-yl-pyridin-3-yl)-amide, 4'-tert-Butyl-6-methyl-biphenyl-3-carboxylic acid (6-azepan-1-yl-pyridin-3-yl)-amide, 6-Methyl-4'-propyl-biphenyl-3-carboxylic acid (6-azepan-1-yl-pyridin-3-yl)-amide, 4'-Isobutyl-6-methyl-biphenyl-3-carboxylic acid (6-azepan-1-yl-pyridin-3-yl)-amide, 4'-Isopropyl-6-methyl-biphenyl-3-carboxylic acid (6-azepan-1-yl-pyridin-3-yl)-amide, 6,2',6'-Trimethyl-biphenyl-3-carboxylic acid (6-azepan-1-yl-pyridin-3-yl)-amide, 6,2',3'-Trimethyl-biphenyl-3-carboxylic acid (6-azepan-1-yl-pyridin-3-yl)-amide, 6-Methyl-4'-trifluoromethyl-biphenyl-3-carboxylic acid (6-azepan-1-yl-pyridin-3-yl)-amide, 6-Methyl-3'-trifluoromethyl-biphenyl-3-carboxylic acid (6-azepan-1-yl-pyridin-3-yl)-amide, 6-Methyl-3',5'-bistrifluoromethyl-biphenyl-3-carboxylic acid (6-azepan-1-yl-pyridin-3-yl)-amide, 3'-Isopropoxy-6-methyl-biphenyl-3-carboxylic acid (6-azepan-1-yl-pyridin-3-yl)-amide, 3'-Ethoxy-6-methyl-biphenyl-3-carboxylic acid (6-azepan-1-yl-pyridin-3-yl)-amide, 2',6'-Dimethoxy-6-methyl-biphenyl-3-carboxylic acid (6-azepan-1-yl-pyridin-3-yl)-amide, 6-Methyl-4'-trifluoromethoxy-biphenyl-3-carboxylic acid (6-azepan-1-yl-pyridin-3-yl)-amide, 6-Methyl-3'-trifluoromethoxy-biphenyl-3-carboxylic acid (6-azepan-1-yl-pyridin-3-yl)-amide, 6-Methyl-biphenyl-3-carboxylic acid (4-morpholin-4-yl-phenyl)-amide, 4'-Methoxy-6-methyl-biphenyl-3-carboxylic acid (4-morpholin-4-yl-phenyl)-amide, 3'-Methoxy-6-methyl-biphenyl-3-carboxylic acid (4-morpholin-4-yl-phenyl)-amide, 4'-(2-Dimethylamino-ethoxy)-6-methyl-biphenyl-3-carboxylic acid (4-morpholin-4-yl-phenyl)-amide, 3'-Dimethylamino-6-methyl-biphenyl-3-carboxylic acid (4-morpholin-4-yl-phenyl)-amide, 4'-Fluoro-6-methyl-biphenyl-3-carboxylic acid (4-morpholin-4-yl-phenyl)-amide, 3'-Fluoro-6-methyl-biphenyl-3-carboxylic acid (4-morpholin-4-yl-phenyl)-amide, 2'-Fluoro-6-methyl-biphenyl-3-carboxylic acid (4-morpholin-4-yl-phenyl)-amide, 4-Methyl-N-(4-morpholin-4-yl-phenyl)-3-quinoxalin-6-yl-benzamide, 6-Methyl-4'-(4-methyl-piperazin-1-yl)-biphenyl-3-carboxylic acid (4-morpholin-4-yl-phenyl)-amide, 2'-Cyano-6-methyl-biphenyl-3-carboxylic acid (4-morpholin-4-yl-phenyl)-amide, 3'-Cyano-6-methyl-biphenyl-3-carboxylic acid (4-morpholin-4-yl-phenyl)-amide, 4'-Cyano-6-methyl-biphenyl-3-carboxylic acid (6-[1,4]oxazepan-4-yl-pyridin-3-yl)-amide, 4'-Cyano-6-methyl-biphenyl-3-carboxylic acid (6-azepan-1-yl-pyridin-3-yl)-amide, 4'-Cyano-6-methyl-biphenyl-3-carboxylic acid [6-(2-methyl-morpholin-4-yl)-pyridin-3-yl]-amide, 4'-Cyano-6-methyl-biphenyl-3-carboxylic acid (3,4,5,6-tetrahydro-2H-[1,2']bipyridinyl-5'-yl)-amide, 4'-Cyano-6-methyl-biphenyl-3-carboxylic acid (6-morpholin-4-yl-pyridin-3-yl)-amide, 4'-Cyano-6-methyl-biphenyl-3-carboxylic acid [6-(4-methyl-piperazin-1-yl)-pyridin-3-yl]-amide, 4'-Cyano-6-methyl-biphenyl-3-carboxylic acid (4-morpholin-4-yl-phenyl)-amide, 4'-Cyano-6-methyl-biphenyl-3-carboxylic acid (3-fluoro-4-morpholin-4-yl-phenyl)-amide, 4'-Cyano-6-methyl-biphenyl-3-carboxylic acid (3-chloro-4-morpholin-4-yl-phenyl)-amide, 4'-Cyano-6-methyl-biphenyl-3-carboxylic acid (3-bromo-4-morpholin-4-yl-phenyl)-amide, 4'-Cyano-6-methyl-biphenyl-3-carboxylic acid (3-methyl-4-morpholin-4-yl-phenyl)-amide, 4'-Cyano-6-methyl-biphenyl-3-carboxylic acid (4-morpholin-4-yl-3-trifluoromethyl-phenyl)-amide, 4'-Cyano-6-methyl-biphenyl-3-carboxylic acid (4-cyclohexyl-phenyl)-amide, 4'-Cyano-6-methyl-biphenyl-3-carboxylic acid biphenyl-4-ylamide, 4'-Cyano-6-methyl-biphenyl-3-carboxylic acid (4'-methoxy-biphenyl-4-yl)-amide, 4'-Cyano-6-methyl-biphenyl-3-carboxylic acid [4-(4-benzyl-piperazin-1-yl)-phenyl]-amide, 4'-Cyano-6-methyl-biphenyl-3-carboxylic acid [4-(piperidine-1-sulfonyl)-phenyl]-amide, 4'-Cyano-6-methyl-biphenyl-3-carboxylic acid [4-(pyrrolidine-1-sulfonyl)-phenyl]-amide, 4'-Cyano-6-methoxy-biphenyl-3-carboxylic acid (6-azepan-1-yl-pyridin-3-yl)-amide, 4'-Cyano-2-methoxy-biphenyl-3-carboxylic acid (6-azepan-1-yl-pyridin-3-yl)-amide, 4'-Cyano-2-methyl-biphenyl-3-carboxylic acid (6-azepan-1-yl-pyridin-3-yl)-amide, 3'-Fluoro-4'-methoxy-6-methyl-biphenyl-3-carboxylic acid (6-azepan-1-yl-pyridin-3-yl)-amide, 4'-Isopropoxy-6-methyl-biphenyl-3-carboxylic acid (6-azepan-1-yl-pyridin-3-yl)-amide, 4'-Butoxy-6-methyl-biphenyl-3-carboxylic acid (6-azepan-1-yl-pyridin-3-yl)-amide, 3'-Chloro-4'-methoxy-6-methyl-biphenyl-3-carboxylic acid (6-azepan-1-yl-pyridin-3-yl)-amide, 4'-Methoxy-6,3'-dimethyl-biphenyl-3-carboxylic acid (6-azepan-1-yl-pyridin-3-yl)-amide, 4'-Cyano-2-methyl-biphenyl-3-carboxylic acid [4-(piperidine-1-sulfonyl)-phenyl]-amide, 4'-Cyano-6-fluoro-biphenyl-3-carboxylic acid [4-(piperidine-1-sulfonyl)-phenyl]-amide, 6-Bromo-4'-cyano-biphenyl-3-carboxylic acid [4-(piperidine-1-sulfonyl)-phenyl]-amide, 4'-Cyano-6-methyl-biphenyl-3-carboxylic acid [6-(4-benzyl-[1,4]diazepan-1-yl)-pyridin-3-yl]-amide, 4'-Cyano-6-methyl-biphenyl-3-carboxylic acid [6-(4-thiophen-3-ylmethyl-[1,4]diazepan-1-yl)-pyridin-3-yl]-amide, 4'-Cyano-2-methyl-biphenyl-3-carboxylic acid [6-(2,6-dimethyl-morpholin-4-yl)-pyridin-3-yl]-amide, 4'-Methoxy-2-methyl-biphenyl-3-carboxylic acid [6-(2,6-dimethyl-morpholin-4-yl)-pyridin-3-yl]-amide, 2-Methyl-4'-trifluoromethyl-biphenyl-3-carboxylic acid [6-(2,6-dimethyl-morpholin-4-yl)-pyridin-3-yl]-amide, 2-Methyl-4'-trifluoromethoxybiphenyl-3-carboxylic acid [6-(2,6-dimethyl-morpholin-4-yl)-pyridin-3-yl]-amide, 4'-Cyano-2-methyl-biphenyl-3-carboxylic acid [6-(2-methyl-morpholin-4-yl)-pyridin-3-yl]-amide, 4'-Cyano-2-fluoro-biphenyl-3-carboxylic acid [4-(piperidine-1-sulfonyl)-phenyl]-amide, 4'-Cyano-6-trifluoromethyl-biphenyl-3-carboxylic acid [4-(piperidine-1-sulfonyl)-phenyl]-amide, 4'-Cyano-6-methyl-biphenyl-3-carboxylic acid [6-(4-pyridin-4-ylmethyl-[1,4]diazepan-1-yl)-pyridin-3-yl]-amide, 4'-Cyano-6-methyl-biphenyl-3-carboxylic acid [6-(4-pyridin-3-ylmethyl-[1,4]diazepan-1-yl)-pyridin-3-yl]-amide, 4'-Cyano-6-methyl-biphenyl-3-carboxylic acid {6-[4-(2,6-dimethoxy-benzyl)-[1,4]diazepan-1-yl]-pyridin-3-yl}-amide, 4'-Cyano-6-methyl-biphenyl-3-carboxylic acid {6-[4-(2-ethoxy-benzyl)-[1,4]diazepan-1-yl]-pyridin-3-yl}-amide, 4'-Cyano-6-methyl-biphenyl-3-carboxylic acid (6-{4-[2-(4-methyl-piperazin-1-yl)-benzyl]-[1,4]diazepan-1-yl}-pyridin-3-yl)-amide, 4'-Cyano-6-methyl-biphenyl-3-carboxylic acid {6-[4-(4-methoxy-2,3-dimethyl-benzyl)-[1,4]diazepan-1-yl]-pyridin-3-yl}-amide, 4'-Cyano-6-methyl-biphenyl-3-carboxylic acid {6-[4-(2,3-dihydro-benzo[1,4]dioxin-6-ylmethyl)-[1,4]diazepan-1-yl]-pyridin-3-yl}-amide, 4'-Cyano-6-methyl-biphenyl-3-carboxylic acid [6-(4-pyridin-2-ylmethyl-[1,4]diazepan-1-yl)-pyridin-3-yl]-amide, 4'-Cyano-6-methyl-biphenyl-3-carboxylic acid [6-(4-benzo[1,3]dioxol-4-ylmethyl-[1,4]diazepan-1-yl)-pyridin-3-yl]-amide, 4'-Cyano-6-methyl-biphenyl-3-carboxylic acid {6-[4-(2-trifluoromethoxy-benzyl)-[1,4]diazepan-1-yl]-pyridin-3-yl}-amide, 4'-Cyano-6-methyl-biphenyl-3-carboxylic acid {6-[4-(2-dimethylamino-benzyl)-[1,4]diazepan-1-yl]-pyridin-3-yl}-amide, 4'-Cyano-6-methyl-biphenyl-3-carboxylic acid {6-[4-(2-chloro-5-trifluoromethyl-benzyl)-[1,4]diazepan-1-yl]-pyridin-3-yl}-amide, 4'-Cyano-6-methyl-biphenyl-3-carboxylic acid {6-[4-(2,3-difluoro-benzyl)-[1,4]diazepan-1-yl]-pyridin-3-yl}-amide, 4'-Cyano-6-methyl-biphenyl-3-carboxylic acid {6-[4-(2-chloro-4-fluoro-benzyl)-[1,4]diazepan-1-yl]-pyridin-3-yl}-amide, 4'-Cyano-6-methyl-biphenyl-3-carboxylic acid {6-[4-(2,6-difluoro-benzyl)-[1,4]diazepan-1-yl]-pyridin-3-yl}-amide, 2-Chloro-4'-cyano-biphenyl-3-carboxylic acid [4-(piperidine-1-sulfonyl)-phenyl]-amide, 4'-Cyano-6-trifluoromethyl-biphenyl-3-carboxylic acid [6-(2,6-dimethyl-morpholin-4-yl)-pyridin-3-yl]-amide, 2-Chloro-4'-cyano-biphenyl-3-carboxylic acid [6-(2,6-dimethyl-morpholin-4-yl)-pyridin-3-yl]-amide, 4'-Cyano-6-ethyl-biphenyl-3-carboxylic acid [6-(2,6-dimethyl-morpholin-4-yl)-pyridin-3-yl]-amide, 4'-Cyano-6-methyl-biphenyl-3-carboxylic acid {6-[4-(3-fluoro-benzyl)-piperazin-1-yl]-pyridin-3-yl}-amide, 4'-Cyano-6-methyl-biphenyl-3-carboxylic acid {6-[4-(2-trifluoromethoxy-benzyl)-piperazin-1-yl]-pyridin-3-yl}-amide, 4'-Cyano-6-methyl-biphenyl-3-carboxylic acid {6-[4-(3-chloro-benzyl)-piperazin-1-yl]-pyridin-3-yl}-amide, 4'-Cyano-6-methyl-biphenyl-3-carboxylic acid {6-[4-(4-isobutyl-benzyl)-piperazin-1-yl]-pyridin-3-yl}-amide, 4'-Cyano-6-methyl-biphenyl-3-carboxylic acid {6-[4-(4-tert-butyl-benzyl)-piperazin-1-yl]-pyridin-3-yl}-amide, 4'-Cyano-6-methyl-biphenyl-3-carboxylic acid {6-[4-(7-methoxy-benzo[1,3]dioxol-5-ylmethyl)-piperazin-1-yl]-pyridin-3-yl}-amide, 4'-Cyano-6-methyl-biphenyl-3-carboxylic acid [6-(4-benzyl-piperazin-1-yl)-pyridin-3-yl]-amide, 4'-Cyano-6-methyl-biphenyl-3-carboxylic acid [6-(4-pyridin-3-ylmethyl-piperazin-1-yl)-pyridin-3-yl]-amide, 4'-Cyano-6-methyl-biphenyl-3-carboxylic acid {6-[4-(4-difluoromethoxy-benzyl)-piperazin-1-yl]-pyridin-3-yl}-amide, 4'-Cyano-6-methyl-biphenyl-3-carboxylic acid {6-[4-(4-cyano-benzyl)-piperazin-1-yl]-pyridin-3-yl}-amide, 4'-Cyano-6-methyl-biphenyl-3-carboxylic acid [6-(4-quinolin-5-ylmethyl-piperazin-1-yl)-pyridin-3-yl]-amide, 4'-Cyano-6-methyl-biphenyl-3-carboxylic acid [6-(4-pyridin-4-ylmethyl-piperazin-1-yl)-pyridin-3-yl]-amide, 4'-Cyano-6-methyl-biphenyl-3-carboxylic acid [6-(4-pyridin-2-ylmethyl-piperazin-1-yl)-pyridin-3-yl]-amide, 4'-Cyano-6-methyl-biphenyl-3-carboxylic acid {6-[4-(4-imidazol-1-yl-benzyl)-piperazin-1-yl]-pyridin-3-yl}-amide, 4'-Cyano-6-methyl-biphenyl-3-carboxylic acid {6-[4-(3-cyano-benzyl)-piperazin-1-yl]-pyridin-3-yl}-amide, 4'-Cyano-6-methyl-biphenyl-3-carboxylic acid [6-(4-isoquinolin-5-ylmethyl-piperazin-1-yl)-pyridin-3-yl]-amide, (R)-2-methyl-N-(6-(2-methylmorpholino)pyridin-3-yl)-4'-(trifluoromethoxy)biphenyl-3-carboxamide, 4'-cyano-2-methyl-N-(6-sulfonylmolpholinopyridin-3-yl)biphenyl-3-carboxamide, (S)-4'-cyano-2-methyl-N-(6-(2-methylmorpholino)pyridin-3-yl)biphenyl-3-carboxamide, (R)-6-chloro-N-(6-(2-methylmorpholino)pyridin-3-yl)-4'-(trifluoromethoxy)biphenyl-3-carboxamide, 4'-cyano-2-methyl-N-(6-sulfinylmorpholinopyridin-3-yl)biphenyl-3-carboxamide, 4'-cyano-N-(6-(diisobutylamino)pyridin-3-yl)-2-methylbiphenyl-3-carboxamide, 4'-cyano-N-(2-((2S,6R)-2,6-dimethylmorpholino)pyrimidin-5-yl)-2-methylbiphenyl-3-carboxamide, N-(2-((2S,6R)-2,6-dimethylmorpholino)pyrimidin-5-yl)-2-methyl-4'-(trifluoromethyl)biphenyl-3-carboxamide, N-(2-((2S,6R)-2,6-dimethylmorpholino)pyrimidin-5-yl)-2-methyl-4'-(trifluoromethoxy)biphenyl-3-carboxamide, N-(2-(bis(2-hydroxyethyl)amino)pyrimidin-5-yl)-2-methyl-4'-(trifluoromethoxy)biphenyl-3-carboxamide, 2-methyl-N-(6-(tetrahydro-2H-pyran-4-yloxy)pyridin-3-yl)-4'-(trifluoromethoxy)biphenyl-3-carboxamide, N-(5-chloro-6-((2S,6R)-2,6-dimethylmorpholino)pyridin-3-yl)-2-methyl-4'-(trifluoromethoxy)biphenyl-3-carboxamide, N-(6-((2R,6S)-2,6-dimethyltetrahydro-2H-pyran-4-yl)pyridin-3-yl)-2-methyl-4'-(trifluoromethoxy)biphenyl-3-carboxamide, N-(6-(4-ethylpiperazine-1-carbonyl)pyridin-3-yl)-2-methyl-4'-(trifluoromethoxy)biphenyl-3-carboxamide, 2-methyl-N-(6-(2-oxopiperazin-1-yl)pyridin-3-yl)-4'-(trifluoromethoxy)biphenyl-3-carboxamide, 2-methyl-N-(6-(1-(pyridin-4-ylmethyl)piperidin-4-yl)pyridin-3-yl)-4'-(trifluoromethoxy)biphenyl-3-carboxamide, 2-methyl-N-(6-(2-oxo-4-(pyridin-4-ylmethyl)piperazin-1-yl)pyridin-3-yl)-4'-(trifluoromethoxy)biphenyl-3-carboxamide, 2-methyl-N-(6-(1-(pyridin-4-ylmethyl)piperidin-3-yl)pyridin-3-yl)-4'-(trifluoromethoxy)biphenyl-3-carboxamide, N-(6-(1-ethylpiperidin-3-yl)pyridin-3-yl)-2-methyl-4'-(trifluoromethoxy)biphenyl-3-carboxamide and N-(6-((2R,6S)-2,6-dimethylmorpholino)pyridin-3-yl)-2-methyl-4'-(trifluoromethoxy)biphenyl-3-carboxamide.

It is, therefore, specifically contemplated that compounds of Formula I which interfere with aspects of hedgehog, Ptc, or smoothened signal transduction activity will likewise be capable of inhibiting proliferation (or other biological consequences) in normal cells and/or cells having a patched loss-of-function phenotype, a hedgehog gain-of-function phenotype, a smoothened gain-of-function phenotype or a Gli gain-of-function phenotype. Thus, it is contemplated that in certain embodiments, these compounds may be useful for inhibiting hedgehog activity in normal cells, e.g., which do not have a genetic mutation that activates the hedgehog pathway. In preferred embodiments, the compounds are capable of inhibiting at least some of the biological activities of hedgehog proteins, preferably specifically in target cells.

Thus, the methods of the present invention include the use of compounds of Formula I which agonize Ptc inhibition of hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In another embodiment, the subject method can be to treat epithelial cells having a phenotype of Ptc loss-of-function, hedgehog gain-of-function, smoothened gain-of-function or Gli gain-of-function. For instance, the subject method can be used in treating or preventing basal cell carcinoma or other hedgehog pathway-related disorders.

In certain embodiments, a compound of Formula I can inhibit activation of a hedgehog pathway by binding to smoothened or its downstream proteins. In certain embodiments, a subject antagonist may inhibit activation of a hedgehog pathway by binding to patched.

In another preferred embodiment, the subject method can be used as part of a treatment regimen for malignant medulloblastomas and other primary CNS malignant neuroectodermal tumors.

In another aspect, the present invention provides pharmaceutical preparations comprising, as an active ingredient, a hedgehog signaling modulator such as a compound of Formula I, a Ptc agonist, a smoothened antagonist, or downstream hedgehog pathway protein antagonist such as described herein, formulated in an amount sufficient to inhibit, in vivo, proliferation or other biological consequences of Ptc loss-of-function, hedgehog gain-of-function, smoothened gain-of-function or Gli gain-of-function.

The subject treatments using a compound of Formula I, patched agonists, smoothened antagonists, or downstream hedgehog pathway protein antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

Pharmacology and Utility

The present invention makes available methods and compounds for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Increased levels of Hedgehog signaling are sufficient to initiate cancer formation and are required for tumor survival. These cancers include, but are not limited to, prostate cancer ("Hedgehog signalling in prostate regeneration, neoplasia and metastasis", Karhadkar S S, Boa G S, Abdallah N, Dhara S, Gardner D, Maitra A, Isaacs J T, Berman D M, Beachy P A., Nature. 2004 Oct. 7; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. 2004 Aug. 24; 101(34):12561-6), breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. 2004 Sep. 1; 64(17):6071-4), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. 2002 Aug. 30; 297(5586):1559-61), basal cell carcinoma ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. 2003 Apr. 15; 100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. 1998 Jan. 1; 391 (6662):90-2), pancreatic cancer ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. 2003 Oct. 23; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. 2003 Oct. 23; 425(6960):846-51), and small-cell lung cancer ("Hedgehog signalling within airway epithelial progenitors and in small-cell lung cancer", Watkins D N, Berman D M, Burkholder S G, Wang B, Beachy P A, Baylin S B., Nature. 2003 Mar. 20; 422(6929):313-7).

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions:

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with immunomodulatory or anti-inflammatory substances or other anti-tumor therapeutic agents. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

Reaction Scheme I:

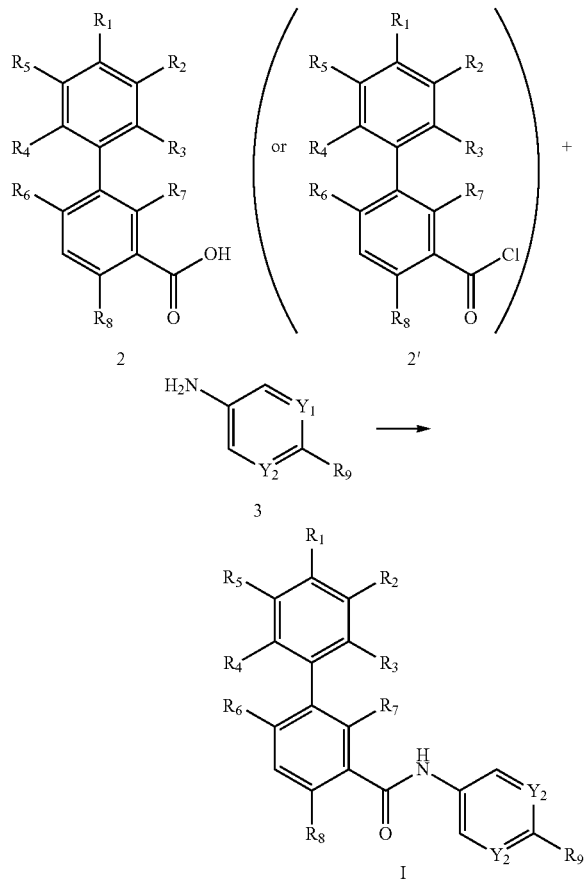

in which $Y_1$, $Y_2$, $R_1$, $R_2$, $R_3$, $R_4$, $R_5$, $R_6$, $R_7$, $R_8$ and $R_9$ are as defined for Formula I in the Summary of the Invention. A compound of Formula I can be prepared by reacting a compound of formula 2 (or 2') with a compound of formula 3 in the presence of a suitable solvent (e.g., dichloromethane, N,N-dimethylformide or the like), in a temperature range of about −20 to about 100° C. The reaction can take up to about 20 hours to complete.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction scheme I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following example that illustrates the preparation of compounds of Formula I according to the invention.

Example 1

4'-cyano-6-methyl-biphenyl-3-carboxylic Acid [4-(morpholine-4-sulfonyl)-phenyl]-amide

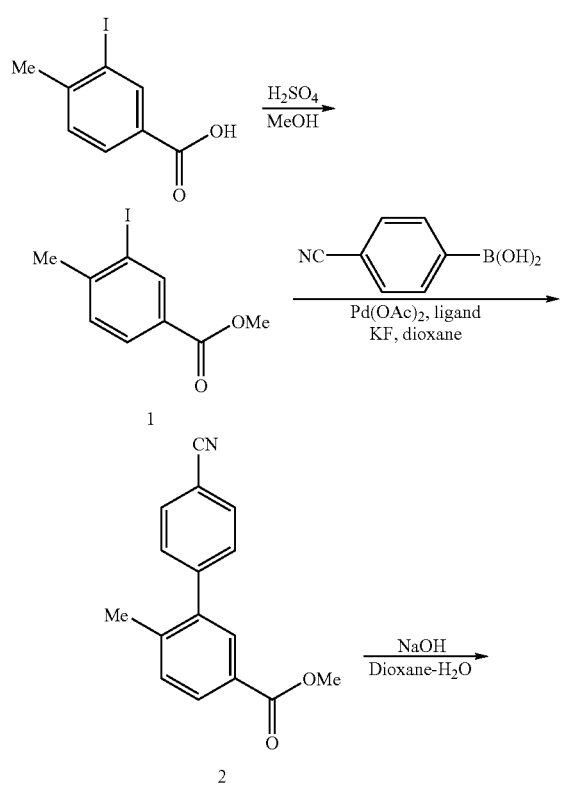

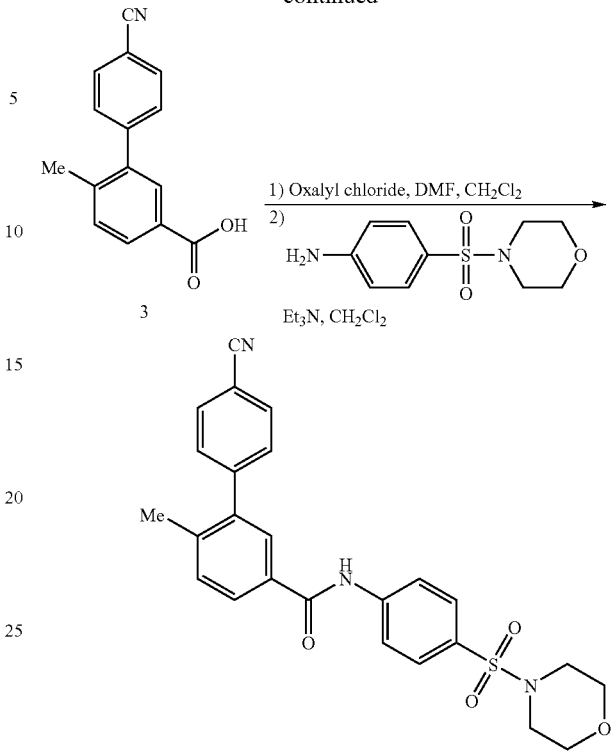

Example 1

Step 1: To a solution of 3-iodo-4-methyl-benzoic acid (10.0 g, 38.2 mmol) in methanol (70 ml) is added concentrated sulfuric acid (0.5 ml). The reaction mixture is heated at 70° C. for 48 hours, cooled to room ambient temperature and then concentrated. After that, ethyl acetate (100 ml) and aqueous $NaHCO_3$ (saturated, 100 ml) solution are added to the residue. The organic layer is separated and washed again with aqueous $NaHCO_3$ (saturated, 100 ml) solution. The organic layer is separated, dried over anhydrous $Na_2SO_4$ and concentrated to yield 3-iodo-4-methyl-benzoic acid methyl ester 1. It is used without further purification in the next step. $^1H$ NMR (400 MHz, DMSO-$d_6$) δ 8.31 (s, 1 H), 7.87 (d, 1 H, J=8.4 Hz), 7.48 (d, 1 H, J=8.4 Hz), 3.85 (s, 3 H), 3.35 (s, 3 H); LC-MS m/z: 277.0 (M+1).

Step 2: To a round-bottom flask containing 3-iodo-4-methyl-benzoic acid methyl ester (1.38 g, 5.00 mmol), 4-cyanophenylboronic acid (1.10 g, 7.48 mmol), palladium acetate (168 mg, 0.748 mmol), 2-(dicyclohexylphosphino)biphenyl (0.526 g, 1.50 mmol) and potassium fluoride (0.870 g, 15.0 mmol) is added anhydrous 1,4-dioxane (15 ml). The flask is purged with argon and sealed. The mixture is stirred at 130° C. for 18 hours, cooled to ambient temperature and then water (20 ml) and ethyl acetate (20 ml) are added. Solid is removed under vacuum filtration. The filtrate is extracted with EtOAc (20 ml×2). The organic layers are combined, washed with aqueous HCl (5%, 20 ml) and saturated $NaHCO_3$ (20 ml). It is dried over $MgSO_4$, and concentrated. The residue is purified by silica gel column chromatography (EtOAc/Hexane, gradient) to give 4'-cyano-6-methyl-biphenyl-3-carboxylic acid methyl ester 2; LC-MS m/z: 252.1 (M+1).

Step 3: To a solution of 4'-cyano-6-methyl-biphenyl-3-carboxylic acid methyl ester 2 (2.56 g, 10.3 mmol) in 1,4-dioxane-$H_2O$ (1:1 mixture, 20 ml) is added NaOH (1.22 g, 30.2 mmol)). The reaction is stirred at ambient temperature for 24 hours. To this mixture is added aqueous HCl (1 N, 36 ml) and it is then extracted with ethyl acetate (40 ml×3). The organic layers are combined, dried over anhydrous Na$_2$SO$_4$. The solver is removed. The solid obtained is washed with small amount of acetonitrile and air dried to give 4'-cyano-6-methyl-biphenyl-3-carboxylic acid 3: $^1$H NMR (DMSO-d$_6$) δ 7.94 (d, 2 H, J=8.0 Hz), 7.84 (dd, 1 H, J$_1$=8.4 Hz, J$_2$=1.2 Hz), 7.75 (d, 1 H, J=1.2 Hz), 7.61 (d, 2 H, J=8.0 Hz), 7.48 (d, 1 H, J=8.4 Hz), 2.29 (s, 3H); LC-MS m/z 238.1 (M+1).

Step 4: To a suspension of 4'-cyano-6-methyl-biphenyl-3-carboxylic acid 3 (40 mg, 0.17 mmol) in anhydrous methylene chloride (5 ml) is added 2 drops of DMF. Then oxalyl chloride (32 mg, 22 μl, 0.25 mmol) is added. The mixture is stirred at ambient temperature until it turns clear. After that, it is concentrated, re-dissolved in anhydrous methylene chloride (3 ml), and added to a solution of 4-(morpholine-4-sulfonyl)-phenylamine (61 mg, 0.25 mmol) and triethylamine (34 mg, 47 t, 0.33 mmol) in methylene chloride (2 ml). The mixture is stirred for 2 hours, concentrated and the residue is purified by preparative mass triggered HPLC (C$_{1-8}$ column, eluted with CH$_3$CN—H$_2$O containing 0.05% TFA) to give 4'-cyano-6-methyl-biphenyl-3-carboxylic acid [4-(morpholine-4-sulfonyl)-phenyl]-amide: $^1$H NMR (DMSO-d$_6$) δ 10.64 (s, 1 H), 8.07 (d, 2 H, J=8.8 Hz), 7.97 (d, 2 H, J=8.4 Hz), 7.95 (d, 1 H, J=8.8 Hz), 7.89 (s, 1 H), 7.43 (d, 2 H, J=8.4 Hz), 7.67 (d, 2 H, J=8.8 Hz), 7.53 (d, 2 H, J=8.8 Hz), 3.63 (m, 4 H), 2.84 (m, 4 H) 2.32 (s, 3 H); LC-MS m/z: 462.1 (M+1).

Example 2

4'-cyano-6-methyl-biphenyl-3-carboxylic Acid [6-(2,6-dimethyl-morpholin-4-yl)-pyridin-3-yl]-amide

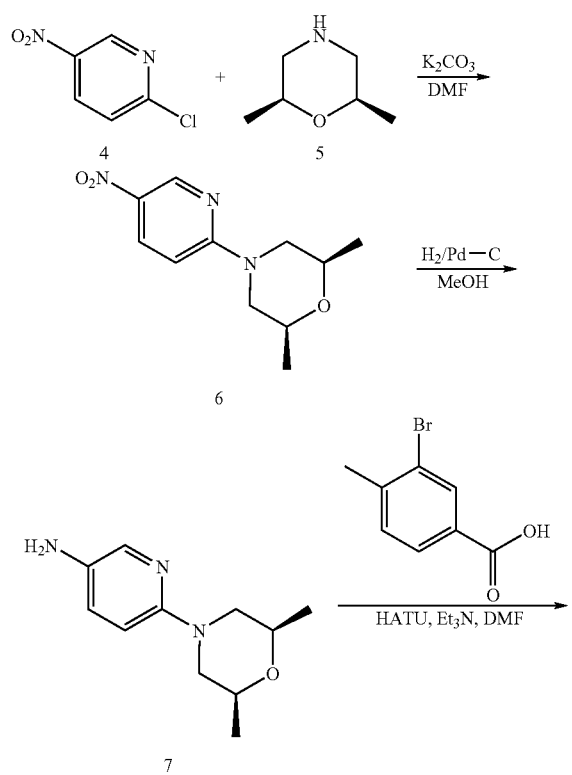

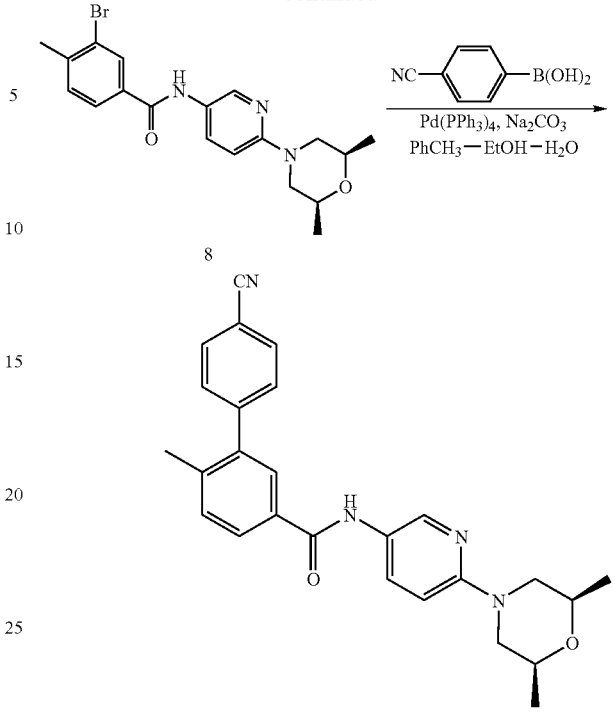

Example 2

Step 1: To a solution of 2-chloro-5-nitro-pyridine 4 (2.38 g, 15 mmoL) and cis-2,6-dimethylmorpholine (1.73 g, 15 mmoL) is added K$_2$CO$_3$ (4.14 g, 30 mmoL). The mixture was heated at 50° C. overnight. After concentration, the residue is partitioned between EtOAc and water. The EtOAc layer is dried over anhydrous Na$_2$SO$_4$ and concentrated to give crude product 6 as a yellow solid. The crude product is used directly in next step without further purification. LC-MS m/z: 238.1 (M+1).

Step 2: The above crude material 6 is hydrogenated in the presence of Pd—C (0.2 g) in MeOH (100 mL) under hydrogen over 10 h. The suspension is filtered through celite and the filtrate is concentrated to give the crude product 7 as a dark brown oil which is used directly in the next step without further purification. LC-MS m/z: 208.1 (M+1).

Step 3: To a solution of 3-bromo-4-methyl benzoic acid (108 mg, 0.5 mmoL), 6-(2,6-Dimethyl-morpholin-4-yl)-pyridin-3-ylamine 7 (104 mg, 0.5 mmoL), and HATU (190 mg, 0.5 mmoL) in dry DMF (5 mL) is added triethylamine (139 uL, 1.0 mmoL) dropwise. The resulting mixture is stirred at room temperature for 2 h. After concentration, the residue is partitioned between EtOAc and water. The organic layer is dried and concentrated to give the crude product. The final compound is purified by flash column chromatography using 50% EtOAc in hexane as eluent to give 8 as a white solid. LC-MS m/z: 404.1 (M+1).

Step 4: A mixture of 4-cyanophenyl boronic acid (18 mg, 0.12 mmol), 3-bromo-N-[6-(2,6-dimethyl-morpholin-4-yl)-pyridin-3-yl]-4-methyl-benzamide 8 (40 mg, 0.1 mmol), Pd(PPh$_3$)$_4$ (11 mg, 0.01 mmol), and Na$_2$CO$_3$ (42 mg, 0.4 mmol) in a combined solvent system of toluene (0.2 mL) and water (0.2 mL) and ethanol (0.05 mL) is heated at 140° C. under microwave irradiation for 30 min. The reaction mixture is diluted with EtOAc and water. The aqueous layer is extracted with EtOAc. The combined organic layer is washed with brine and concentrated to give the crude product which is purified by preparative mass triggered HPLC (C$_{18}$ column, eluted with CH$_3$CN—H$_2$O containing 0.05% TFA) to give 4'-cyano-6-methyl-biphenyl-3-carboxylic acid [6-(2,6-dimethyl-morpholin-4-yl)-pyridin-3-yl]-amide. LC-MS m/z: 427.2 (M+1).

By repeating the procedures described in the above examples, using appropriate starting materials, the following compounds of Formula I, as identified in Table 1, are obtained.

TABLE 1

| Compound Number | Structure | Physical Data MS (m/z) |
|---|---|---|
| 3 | 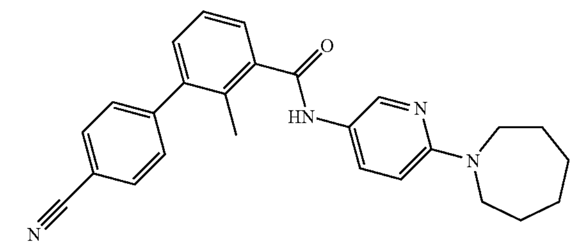 | LC-MS m/z 411.2 (M + 1). |
| 4 | 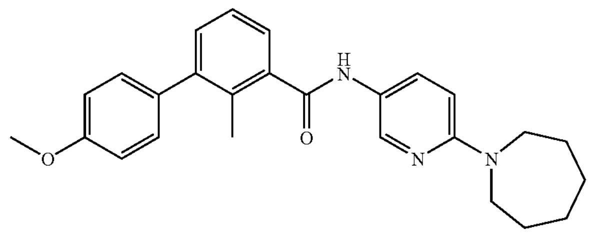 | LC-MS m/z 416.2 (M + 1). |
| 5 | 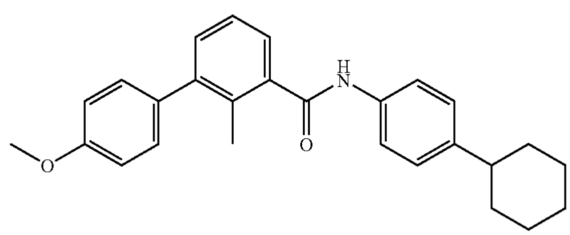 | LC-MS m/z 400.2 (M + 1). |
| 6 | 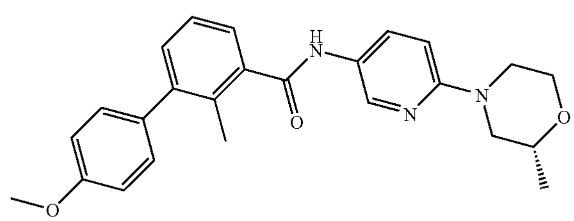 | LC-MS m/z 418.2 (M + 1). |
| 7 | 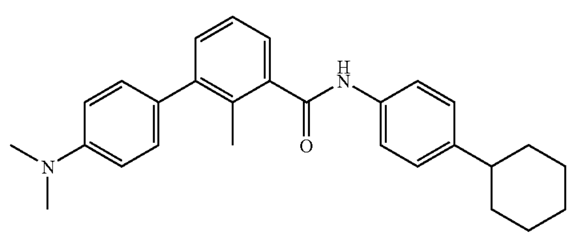 | LC-MS m/z 413.2 (M + 1). |
| 8 | 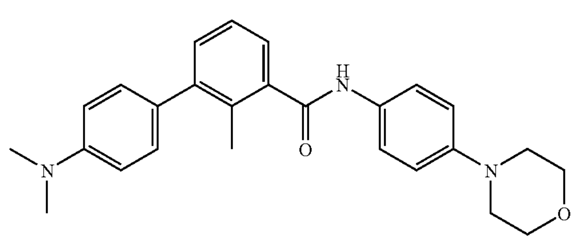 | LC-MS m/z 416.2 (M + 1). |

TABLE 1-continued

| Compound Number | Structure | Physical Data MS (m/z) |
|---|---|---|
| 9 | 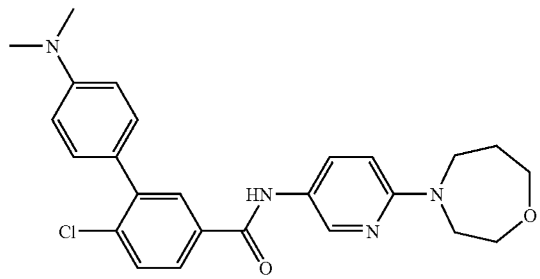 | LC-MS m/z 451.2 (M + 1). |
| 10 | 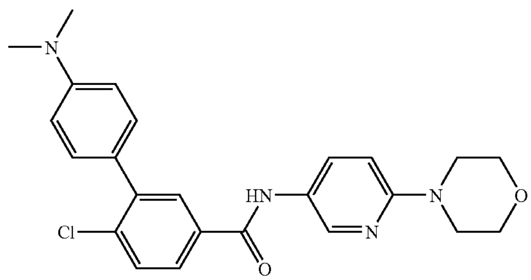 | LC-MS m/z 437.2 (M + 1). |
| 11 | 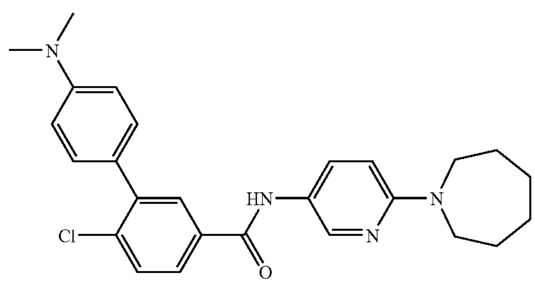 | LC-MS m/z 449.2 (M + 1). |
| 12 | 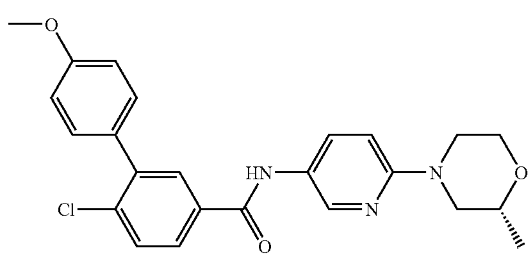 | LC-MS m/z 438.2 (M + 1). |
| 13 | 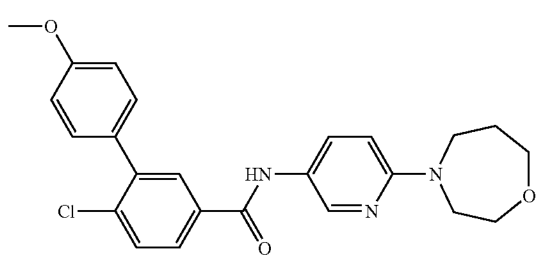 | LC-MS m/z 438.2 (M + 1). |

TABLE 1-continued

| Compound Number | Structure | Physical Data MS (m/z) |
|---|---|---|
| 14 | 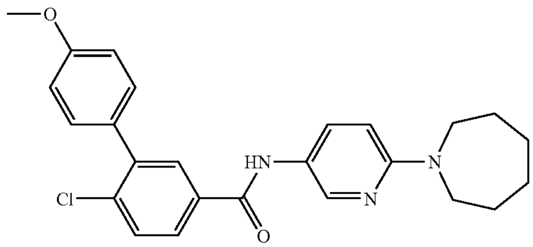 | LC-MS m/z 436.2 (M + 1). |
| 15 | 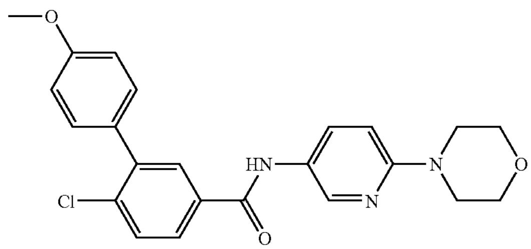 | LC-MS m/z 424.1 (M + 1). |
| 16 | 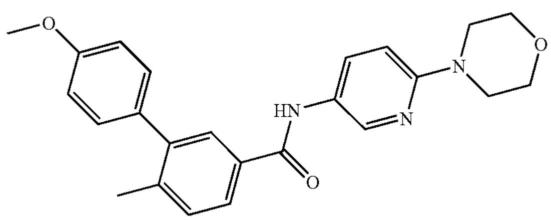 | LC-MS m/z 404.2 (M + 1). |
| 17 | 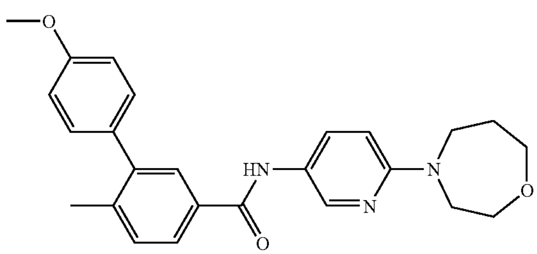 | LC-MS m/z 418.2 (M + 1). |
| 18 | 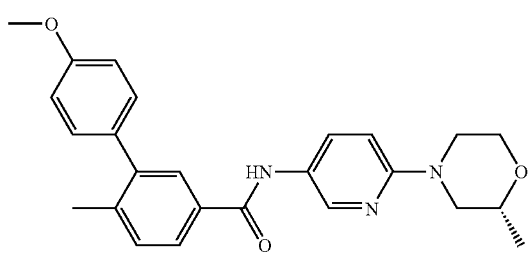 | LC-MS m/z 418.2 (M + 1). |
| 19 | 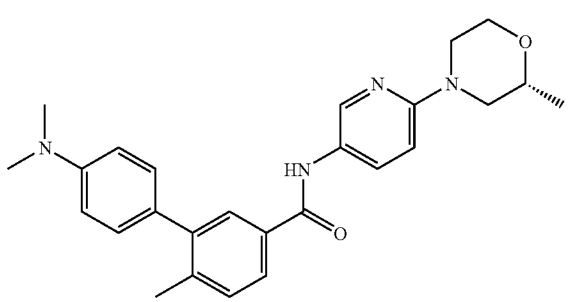 | LC-MS m/z 431.2 (M + 1). |

TABLE 1-continued

| Compound Number | Structure | Physical Data MS (m/z) |
|---|---|---|
| 20 | 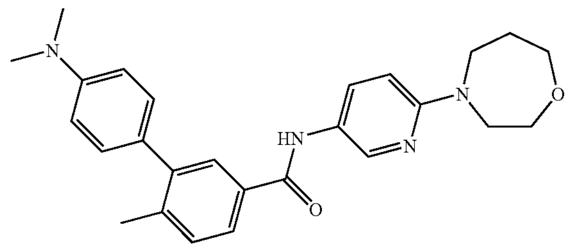 | LC-MS m/z 431.2 (M + 1). |
| 21 | 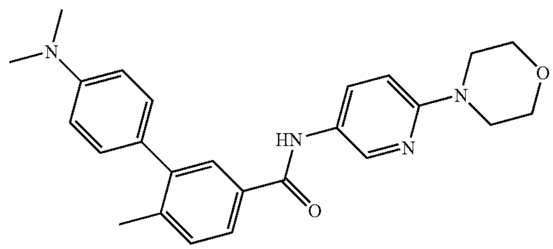 | LC-MS m/z 417.2 (M + 1). |
| 22 | 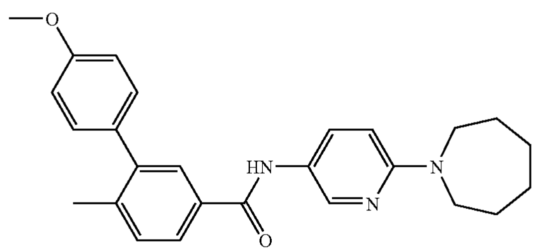 | LC-MS m/z 416.2 (M + 1). |
| 23 | 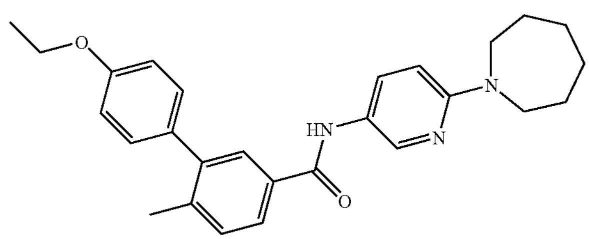 | LC-MS m/z 430.2 (M + 1). |
| 24 | 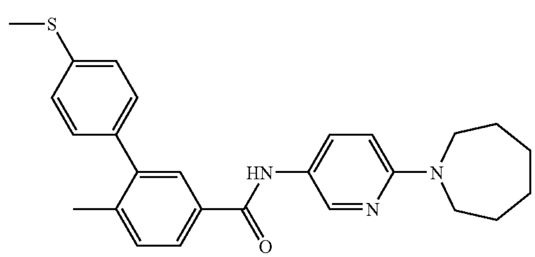 | LC-MS m/z 432.2 (M + 1). |
| 25 | 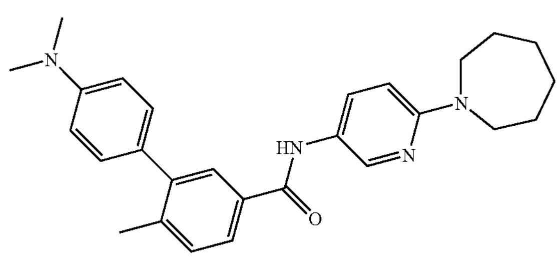 | LC-MS m/z 429.2 (M + 1). |

TABLE 1-continued

| Compound Number | Structure | Physical Data MS (m/z) |
|---|---|---|
| 26 | 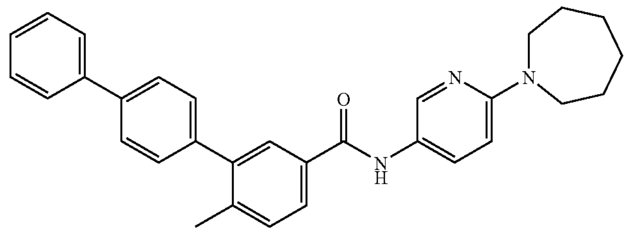 | LC-MS m/z 462.2 (M + 1). |
| 27 | 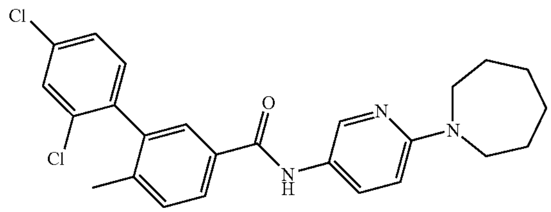 | LC-MS m/z 454.1 (M + 1). |
| 28 | 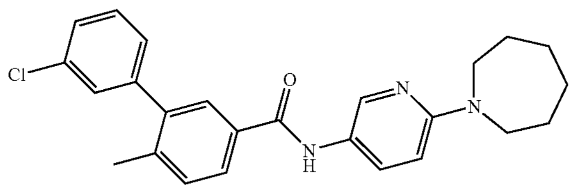 | LC-MS m/z 420.2 (M + 1). |
| 29 | 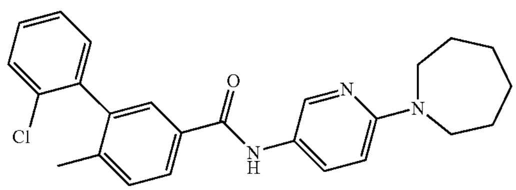 | LC-MS m/z 420.2 (M + 1). |
| 30 | 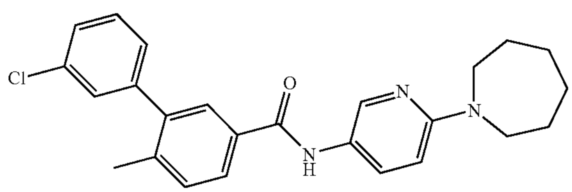 | LC-MS m/z 420.2 (M + 1). |
| 31 | 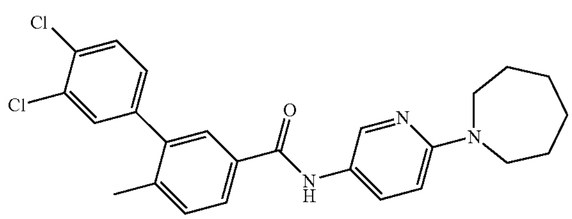 | LC-MS m/z 454.2 (M + 1). |
| 32 | 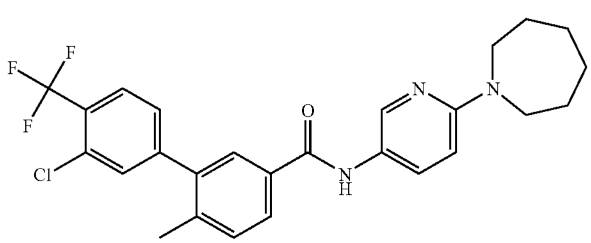 | LC-MS m/z 488.1 (M + 1). |

TABLE 1-continued

| Compound Number | Structure | Physical Data MS (m/z) |
|---|---|---|
| 33 | 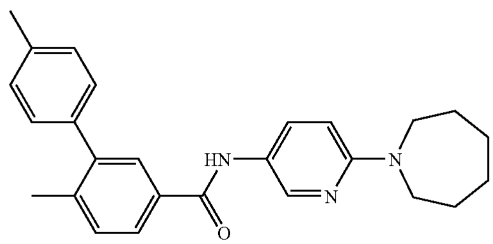 | LC-MS m/z 400.2 (M + 1). |
| 34 | 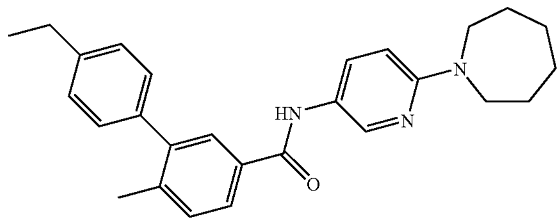 | LC-MS m/z 414.2 (M + 1). |
| 35 | 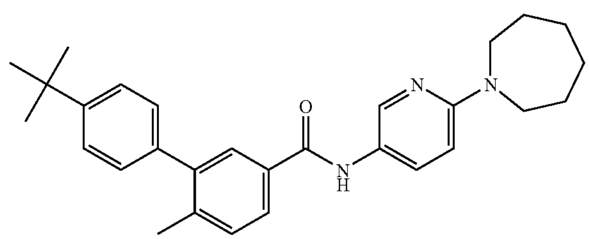 | LC-MS m/z 442.2 (M + 1). |
| 36 | 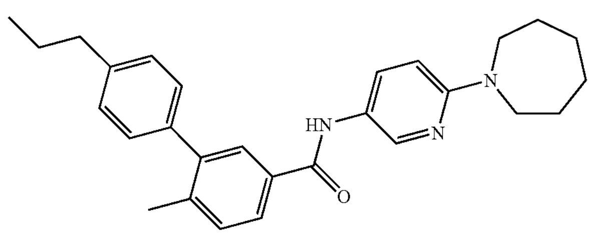 | LC-MS m/z 428.2 (M + 1). |
| 37 | 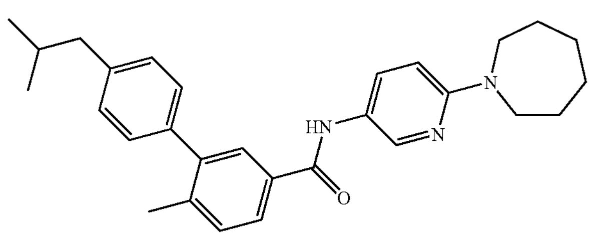 | LC-MS m/z 442.2 (M + 1). |
| 38 | 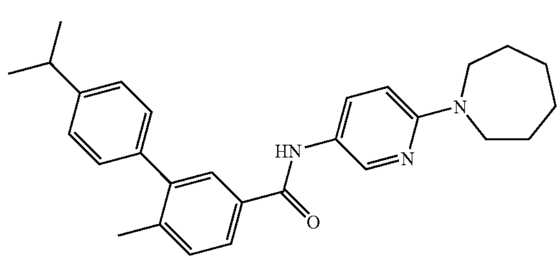 | LC-MS m/z 428.2 (M + 1). |

TABLE 1-continued

| Compound Number | Structure | Physical Data MS (m/z) |
|---|---|---|
| 39 | 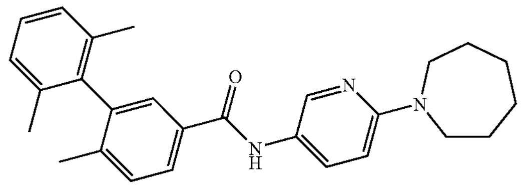 | LC-MS m/z 414.2 (M + 1). |
| 40 | 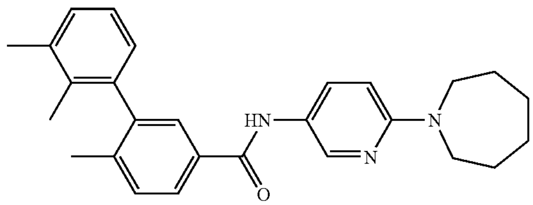 | LC-MS m/z 414.2 (M + 1). |
| 41 | 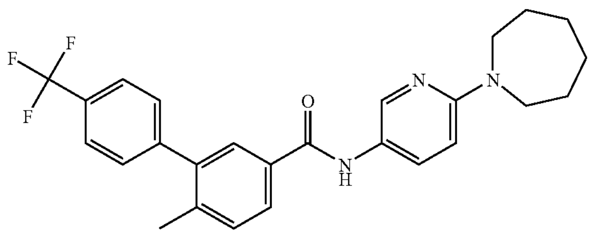 | LC-MS m/z 454.2 (M + 1). |
| 42 | 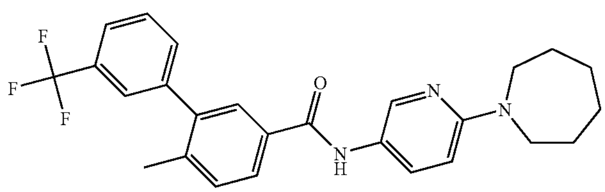 | LC-MS m/z 454.2 (M + 1). |
| 43 | 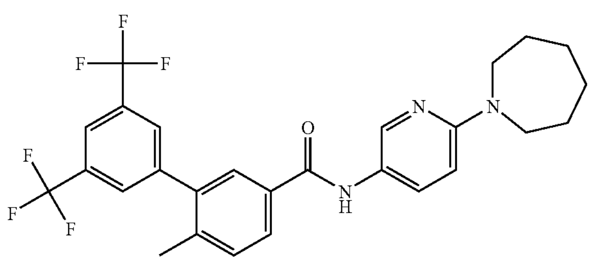 | LC-MS m/z 522.2 (M + 1). |
| 44 | 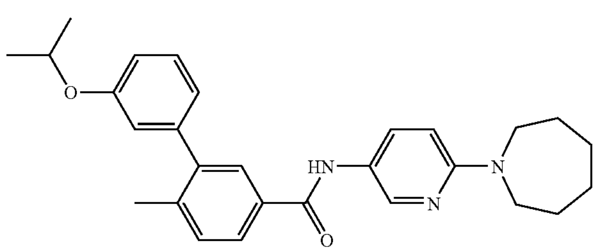 | LC-MS m/z 444.2 (M + 1). |
| 45 | 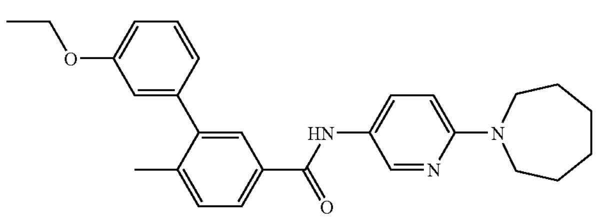 | LC-MS m/z 430.2 (M + 1). |

TABLE 1-continued

| Compound Number | Structure | Physical Data MS (m/z) |
|---|---|---|
| 46 | 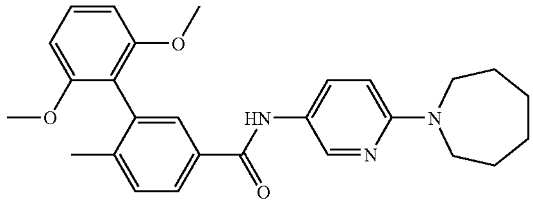 | LC-MS m/z 446.2 (M + 1). |
| 47 | 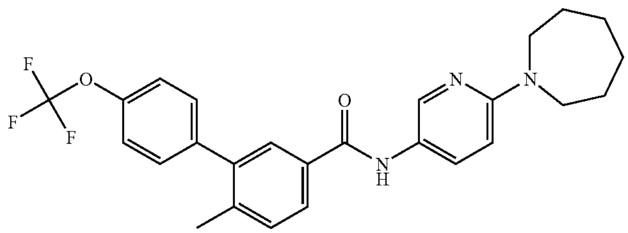 | LC-MS m/z 470.2 (M + 1). |
| 48 | 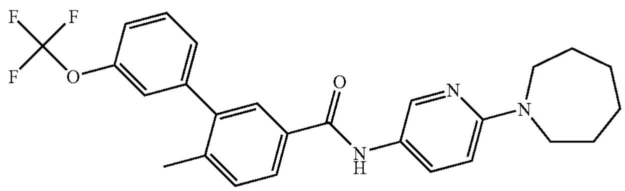 | LC-MS m/z 470.2 (M + 1). |
| 49 | 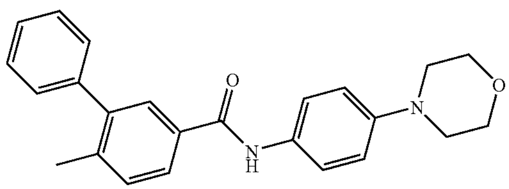 | LC-MS m/z 373.2 (M + 1). |
| 50 | 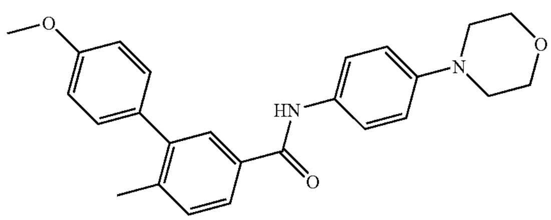 | LC-MS m/z 403.2 (M + 1). |
| 51 | 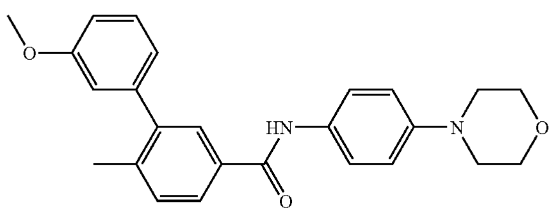 | LC-MS m/z 403.2 (M + 1). |
| 52 | 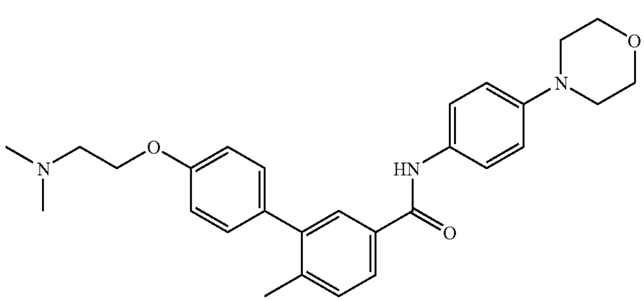 | LC-MS m/z 460.2 (M + 1). |

TABLE 1-continued

| Compound Number | Structure | Physical Data MS (m/z) |
|---|---|---|
| 53 | 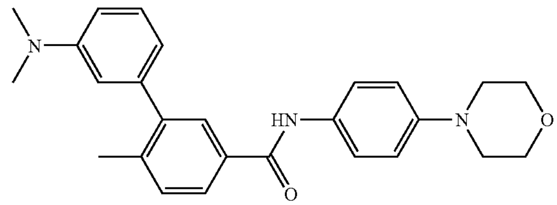 | LC-MS m/z 416.2 (M + 1). |
| 54 | 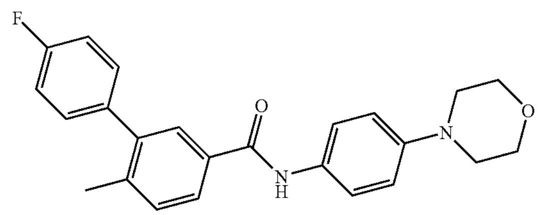 | LC-MS m/z 391.2 (M + 1). |
| 55 | 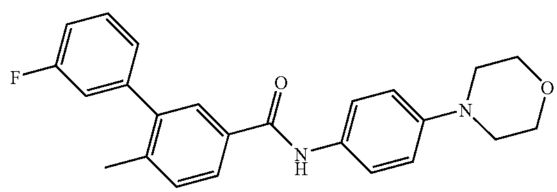 | LC-MS m/z 391.2 (M + 1). |
| 56 | 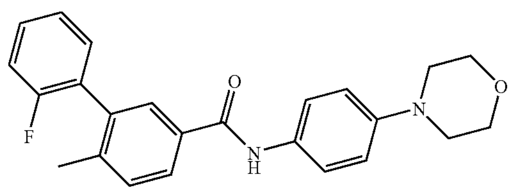 | LC-MS m/z 391.2 (M + 1). |
| 57 | 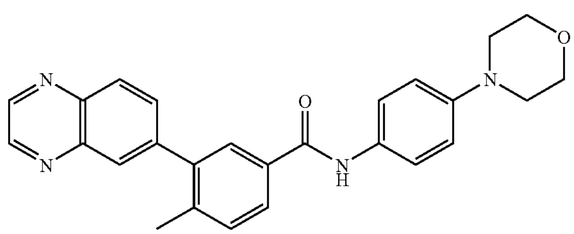 | LC-MS m/z 425.2 (M + 1). |
| 58 | 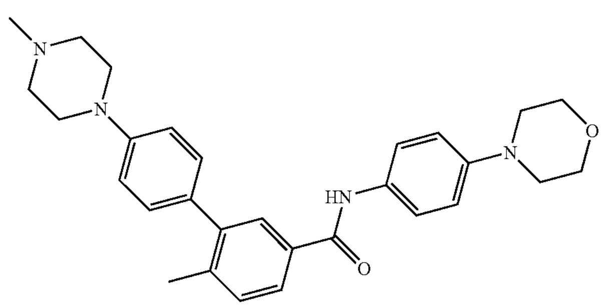 | LC-MS m/z 471.2 (M + 1). |
| 59 | 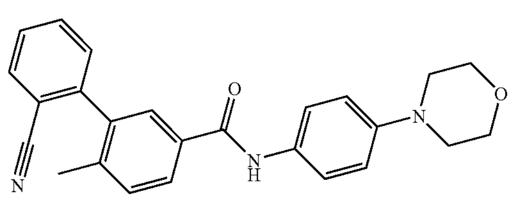 | LC-MS m/z 398.2 (M + 1). |

TABLE 1-continued
| Compound Number | Structure | Physical Data MS (m/z) |
|---|---|---|
| 60 | 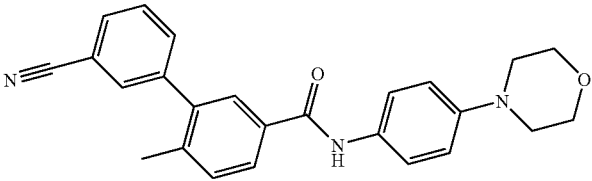 | LC-MS m/z 398.2 (M + 1). |
| 61 | 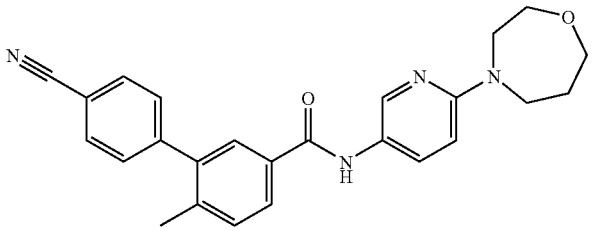 | LC-MS m/z 413.2 (M + 1). |
| 62 | 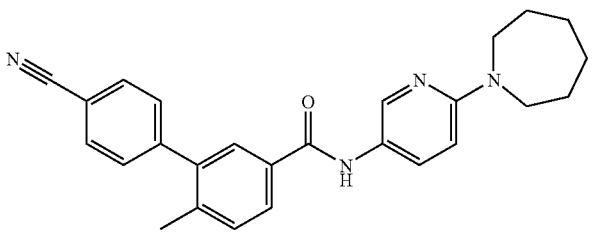 | LC-MS m/z 411.2 (M + 1). |
| 63 | 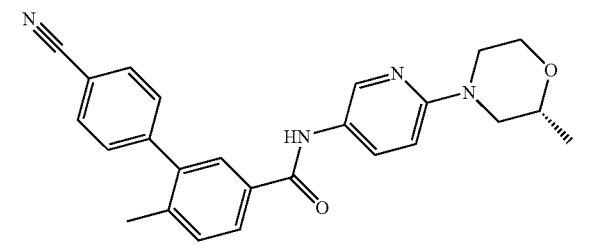 | LC-MS m/z 413.2 (M + 1). |
| 64 | 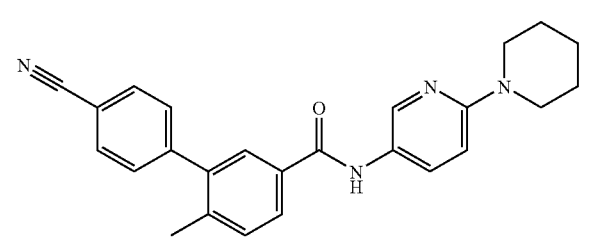 | LC-MS m/z 397.2 (M + 1). |
| 65 | 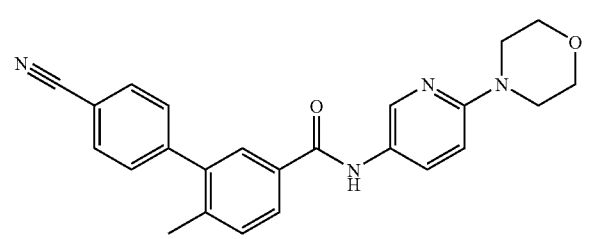 | LC-MS m/z 399.2 (M + 1). |

TABLE 1-continued

| Compound Number | Structure | Physical Data MS (m/z) |
|---|---|---|
| 66 | 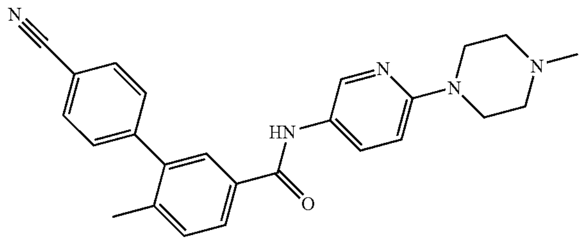 | LC-MS m/z 412.2 (M + 1). |
| 67 | 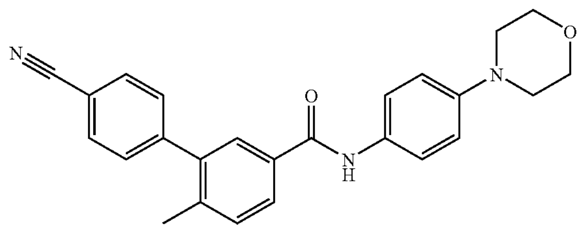 | LC-MS m/z 398.2 (M + 1). |
| 68 | 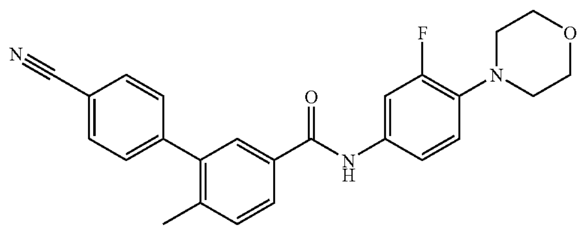 | LC-MS m/z 416.2 (M + 1). |
| 69 | 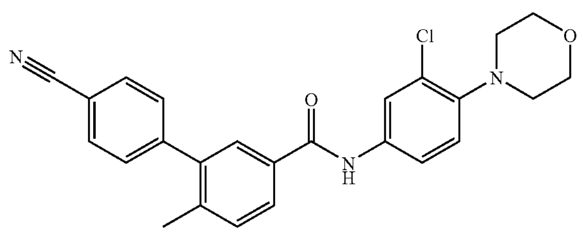 | LC-MS m/z 432.1 (M + 1). |
| 70 | 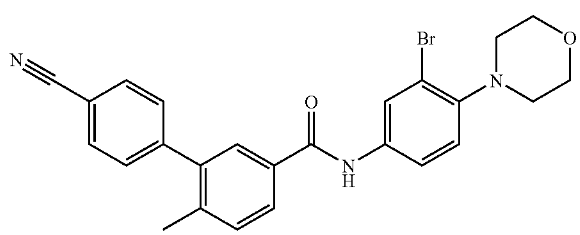 | LC-MS m/z 476.1 (M + 1). |
| 71 | 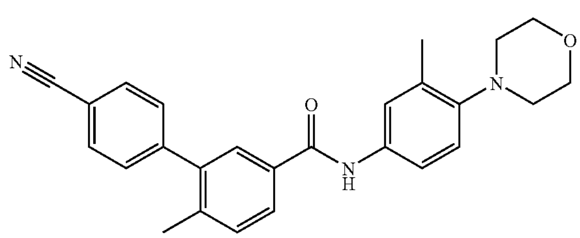 | LC-MS m/z 412.2 (M + 1). |

TABLE 1-continued

| Compound Number | Structure | Physical Data MS (m/z) |
|---|---|---|
| 72 | 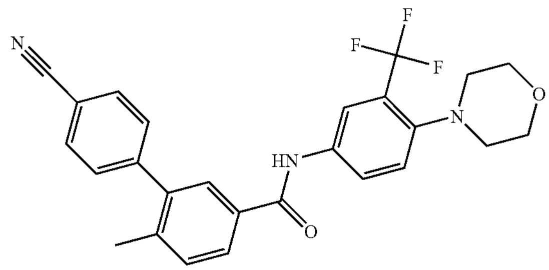 | LC-MS m/z 466.2 (M + 1). |
| 73 | 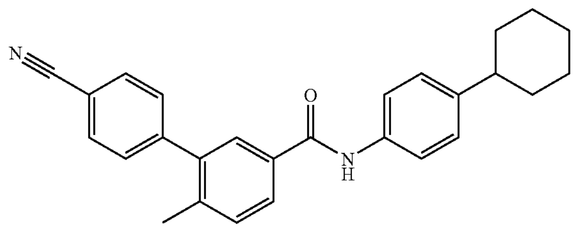 | LC-MS m/z 385.2 (M + 1). |
| 74 | 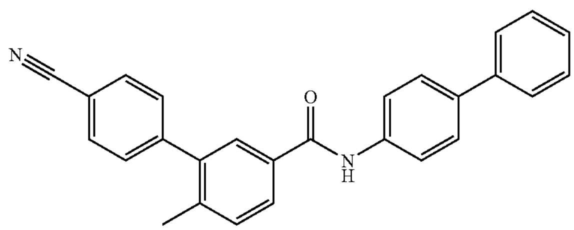 | LC-MS m/z 389.1 (M + 1). |
| 75 | 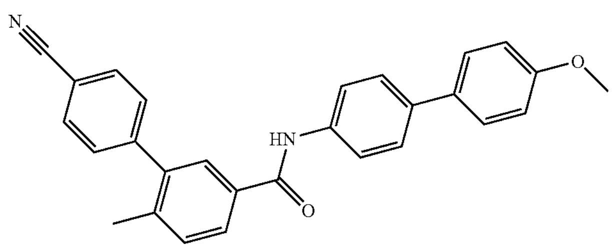 | LC-MS m/z 419.2 (M + 1). |
| 76 | 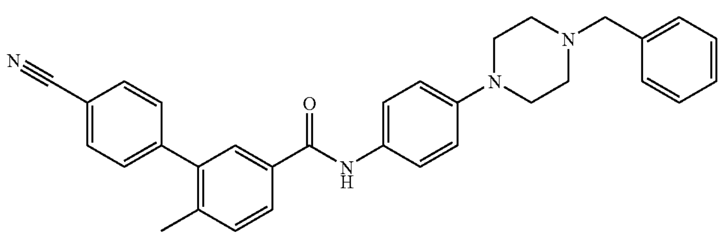 | LC-MS m/z 487.2 (M + 1). |
| 77 | 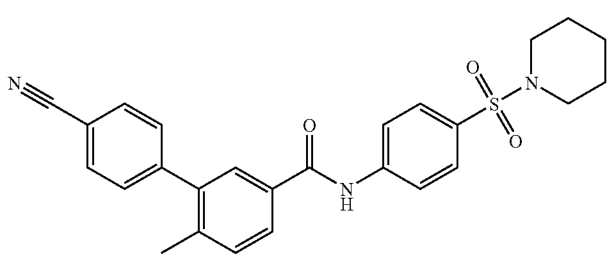 | LC-MS m/z 460.2 (M + 1). |

TABLE 1-continued

| Compound Number | Structure | Physical Data MS (m/z) |
|---|---|---|
| 78 | 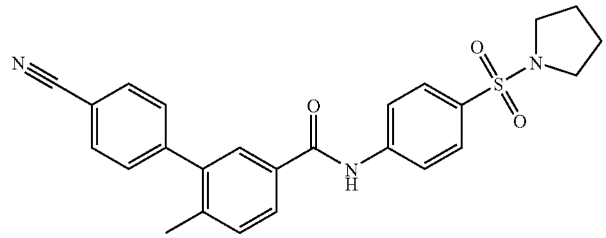 | LC-MS m/z 446.1 (M + 1). |
| 79 | 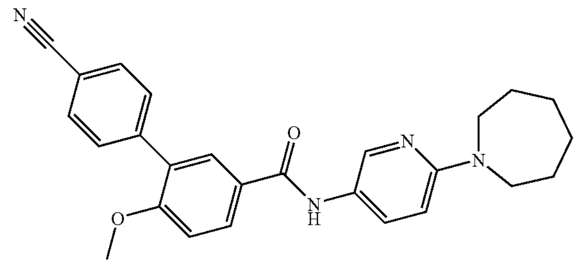 | LC-MS m/z 427.2 (M + 1). |
| 80 | 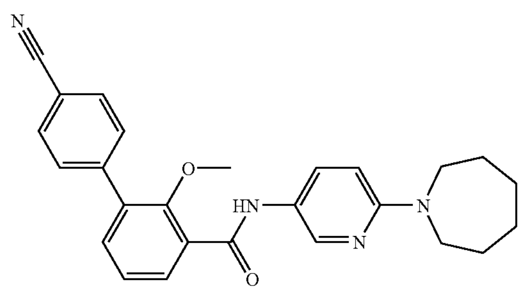 | LC-MS m/z 427.2 (M + 1) |
| 81 | 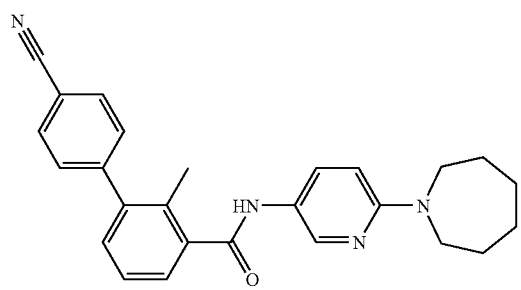 | LC-MS m/z 411.2 (M + 1) |
| 82 | 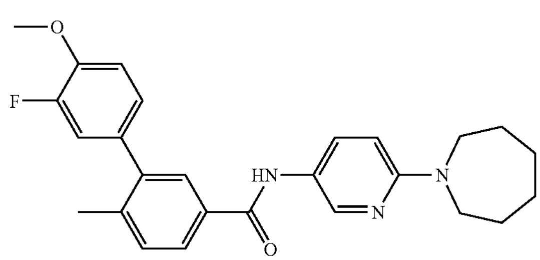 | LC-MS m/z 434.2 (M + 1) |

TABLE 1-continued

| Compound Number | Structure | Physical Data MS (m/z) |
|---|---|---|
| 83 | 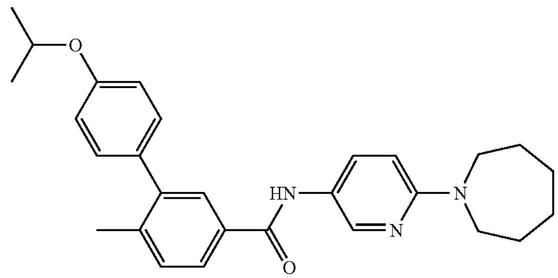 | LC-MS m/z 444.3 (M + 1) |
| 84 | 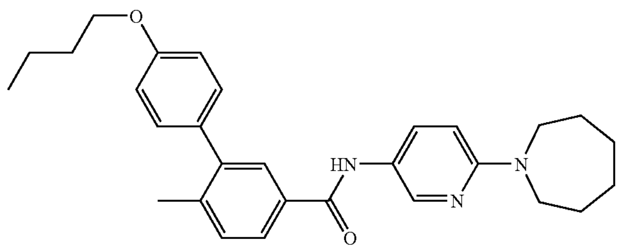 | LC-MS m/z 458.3 (M + 1) |
| 85 | 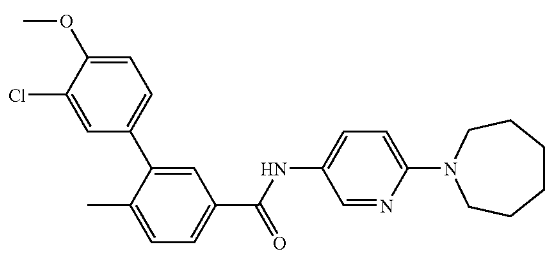 | LC-MS m/z 450.2 (M + 1) |
| 86 | 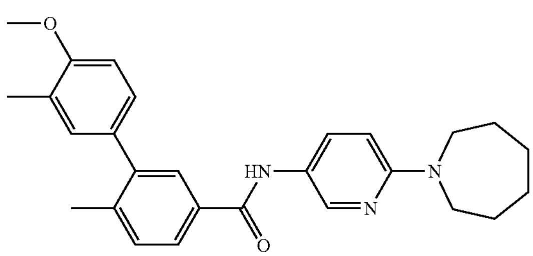 | LC-MS m/z 430.2 (M + 1) |
| 87 | 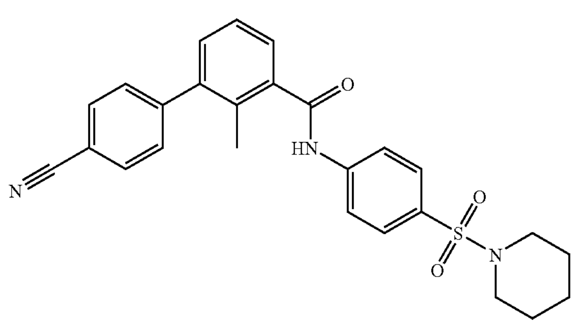 | LC-MS m/z 460.2 (M + 1) |

TABLE 1-continued

| Compound Number | Structure | Physical Data MS (m/z) |
|---|---|---|
| 88 | 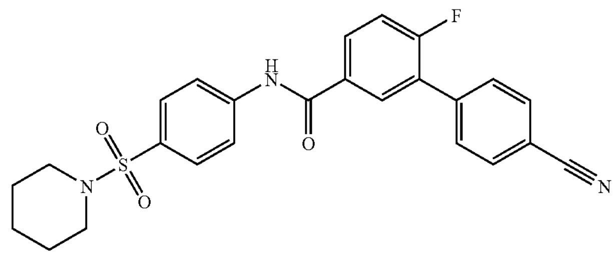 | LC-MS m/z 464.1 (M + 1) |
| 89 | 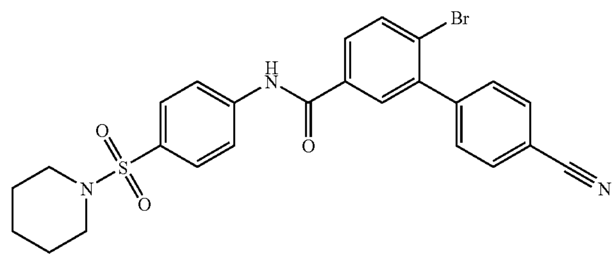 | LC-MS m/z 524.1 (M + 1) |
| 90 | 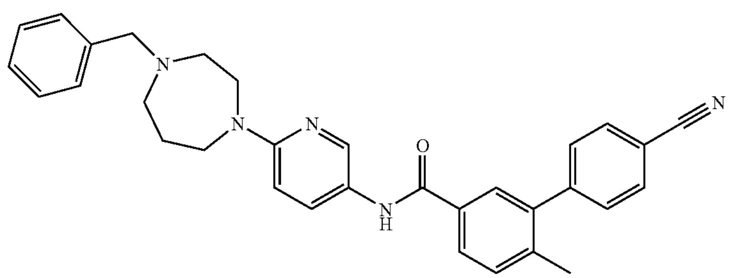 | LC-MS m/z 502.3 (M + 1) |
| 91 | 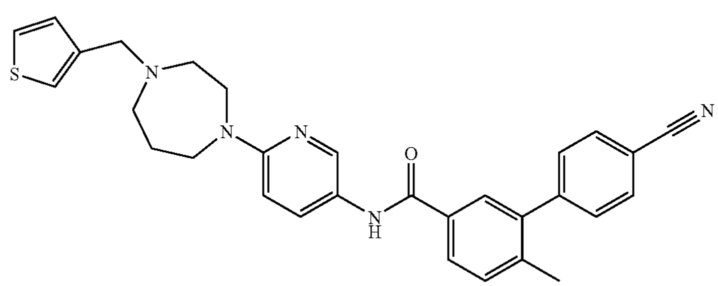 | LC-MS m/z 508.2 (M + 1) |
| 92 | 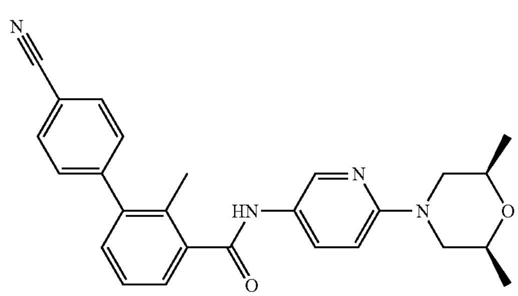 | LC-MS m/z 427.2 (M + 1) |

TABLE 1-continued

| Compound Number | Structure | Physical Data MS (m/z) |
|---|---|---|
| 93 | 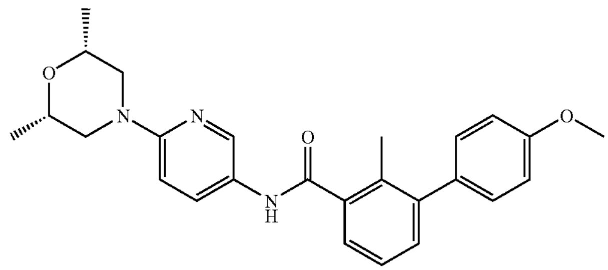 | LC-MS m/z 432.2 (M + 1) |
| 94 | 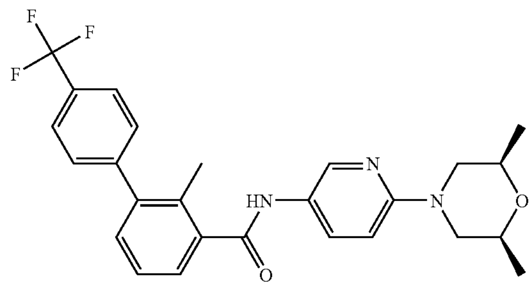 | LC-MS m/z 470.2 (M + 1) |
| 95 | 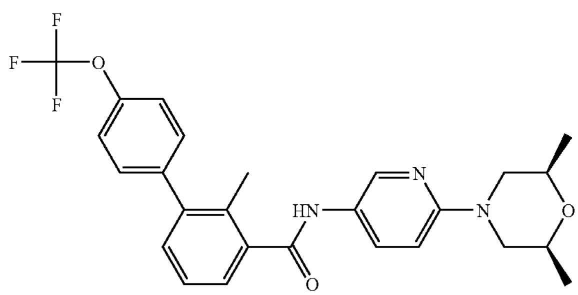 | LC-MS m/z 486.2 (M + 1) |
| 96 | 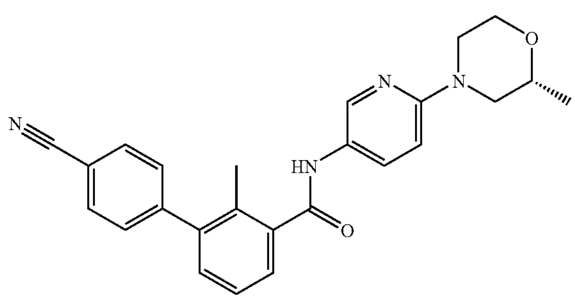 | LC-MS m/z 413.2 (M + 1) |
| 97 | 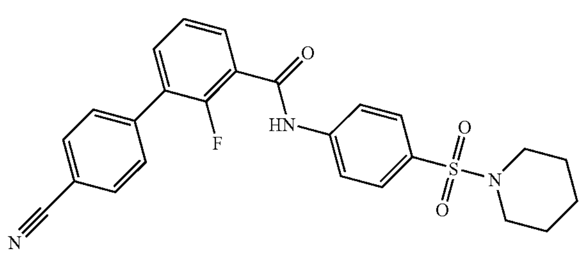 | LC-MS m/z 464.1 (M + 1) |

TABLE 1-continued

| Compound Number | Structure | Physical Data MS (m/z) |
|---|---|---|
| 98 | 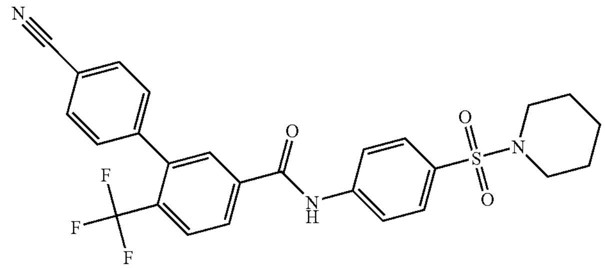 | LC-MS m/z 514.1 (M + 1) |
| 99 | 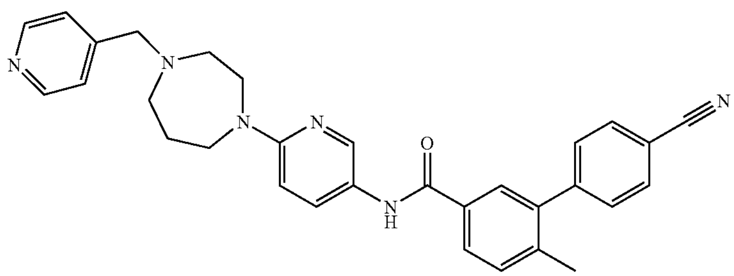 | LC-MS m/z 503.3 (M + 1) |
| 100 | 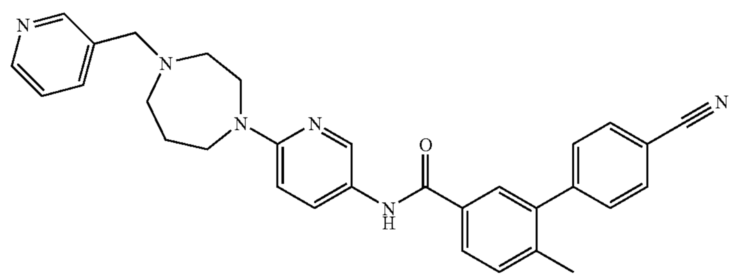 | LC-MS m/z 503.3 (M + 1) |
| 101 | 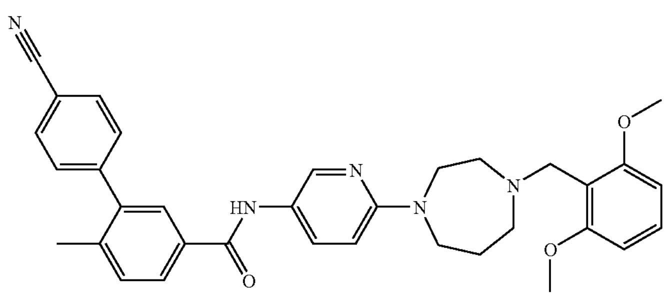 | LC-MS m/z 562.3 (M + 1) |
| 102 | 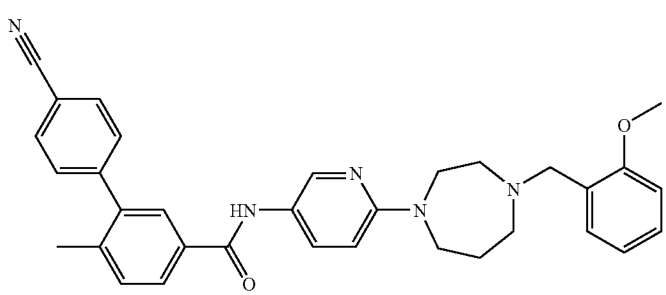 | LC-MS m/z 546.3 (M + 1) |

TABLE 1-continued

| Compound Number | Structure | Physical Data MS (m/z) |
| --- | --- | --- |
| 103 | 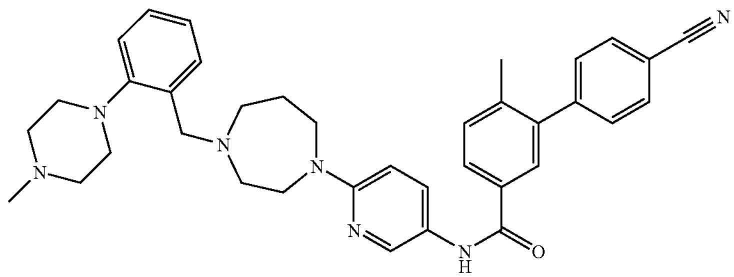 | LC-MS m/z 600.3 (M + 1) |
| 104 | 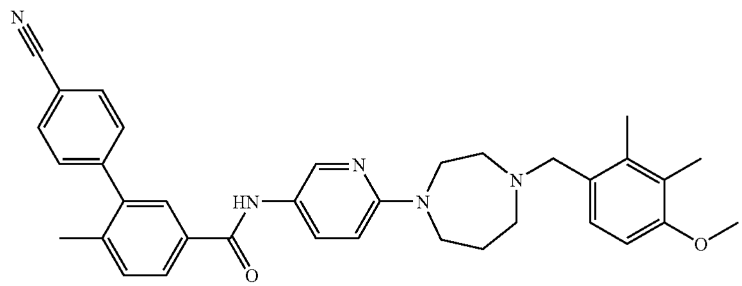 | LC-MS m/z 560.3 (M + 1) |
| 105 | 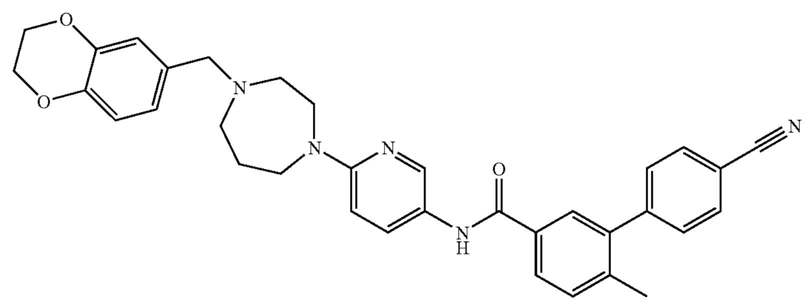 | LC-MS m/z 560.3 (M + 1) |
| 106 | 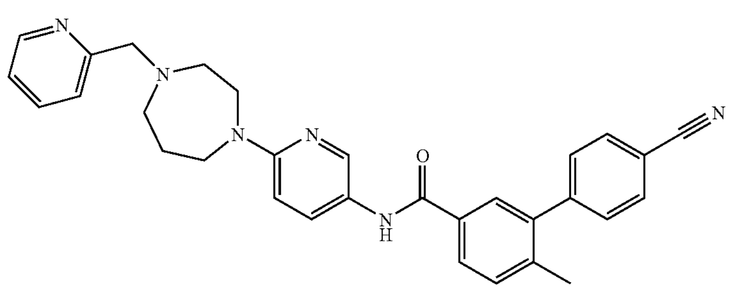 | LC-MS m/z 503.3 (M + 1) |
| 107 | 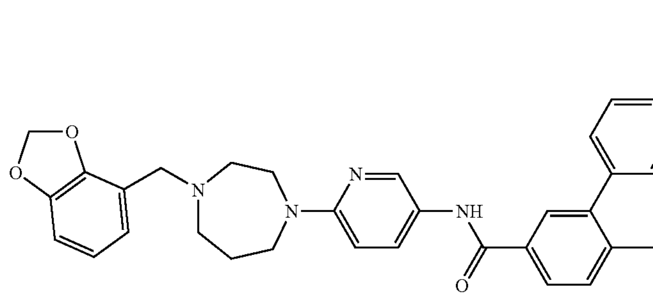 | LC-MS m/z 546.2 (M + 1) |

TABLE 1-continued

| Compound Number | Structure | Physical Data MS (m/z) |
|---|---|---|
| 108 | 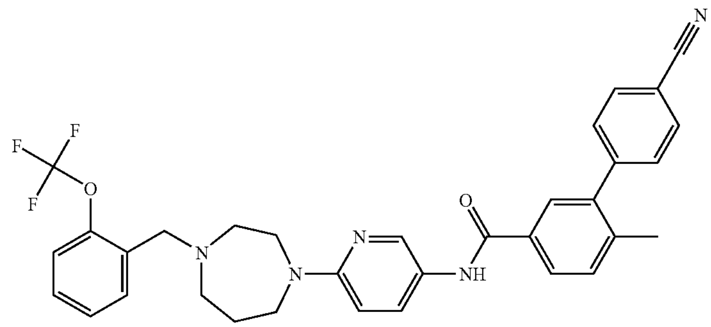 | LC-MS m/z 586.2 (M + 1) |
| 109 | 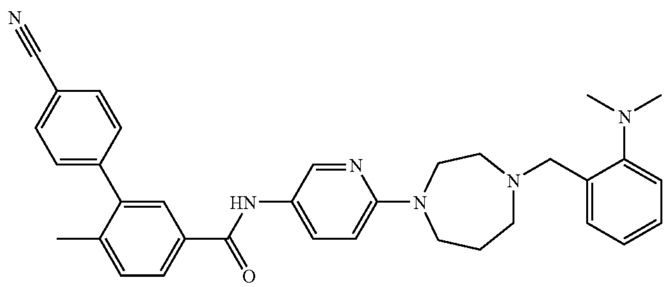 | LC-MS m/z 545.3 (M + 1) |
| 110 | 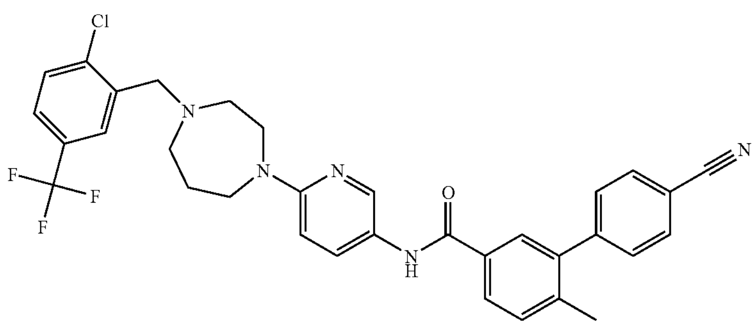 | LC-MS m/z 604.2 (M + 1) |
| 111 | 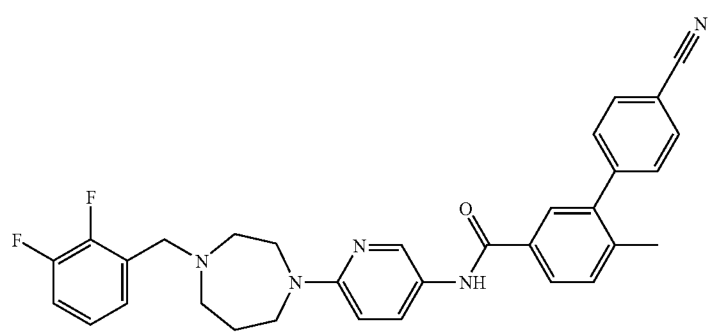 | LC-MS m/z 538.2 (M + 1) |
| 112 | 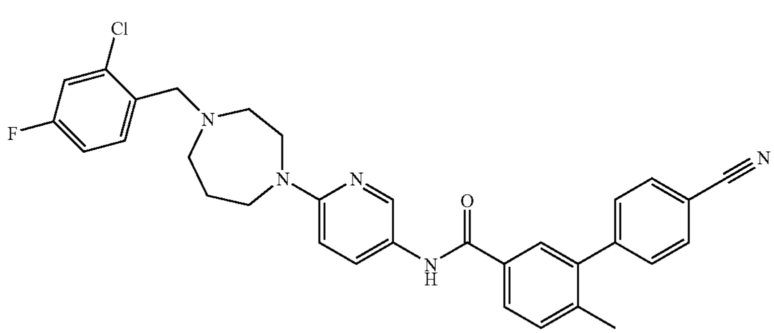 | LC-MS m/z 554.2 (M + 1) |

TABLE 1-continued

| Compound Number | Structure | Physical Data MS (m/z) |
| --- | --- | --- |
| 113 | 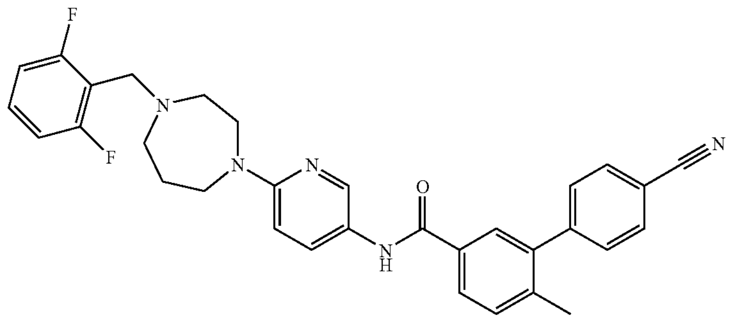 | LC-MS m/z 538.2 (M + 1) |
| 114 | 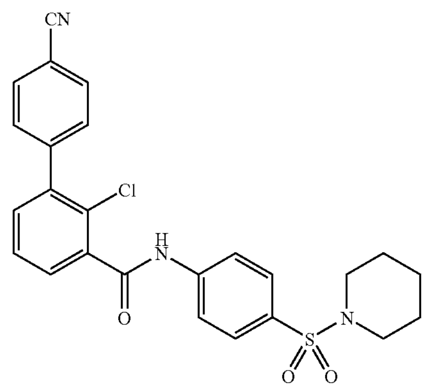 | LC-MS m/z 480.1 (M + 1) |
| 115 | 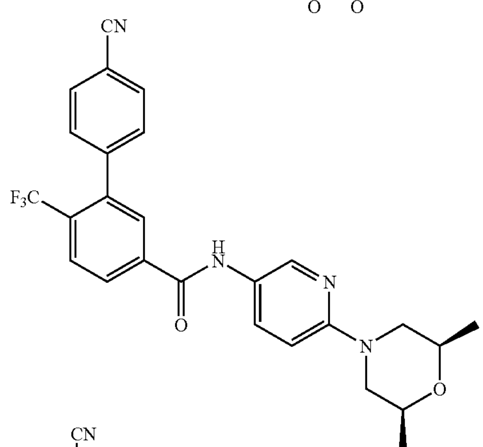 | LC-MS m/z 481.2 (M + 1) |
| 116 | 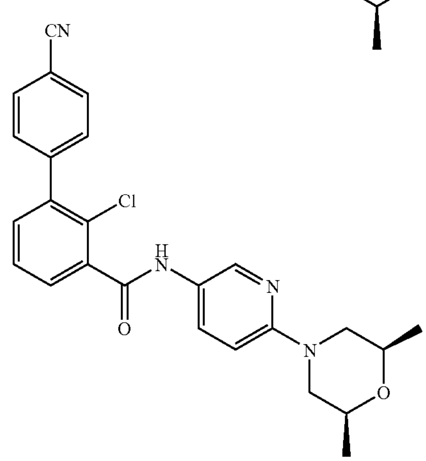 | LC-MS m/z 447.2 (M + 1) |

TABLE 1-continued

| Compound Number | Structure | Physical Data MS (m/z) |
|---|---|---|
| 117 | 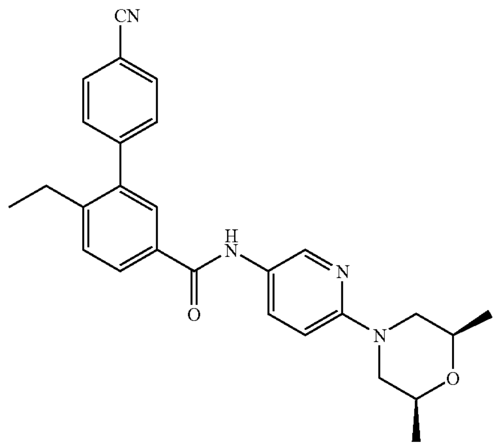 | LC-MS m/z 441.2 (M + 1) |
| 118 | 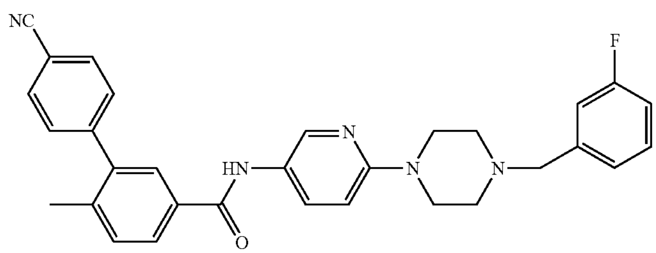 | LC-MS m/z 506.2 (M + 1) |
| 119 | 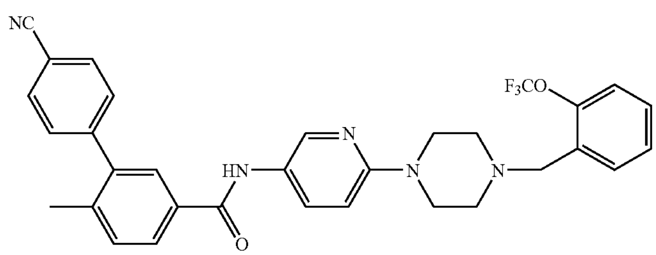 | LC-MS m/z 572.2 (M + 1) |
| 120 | 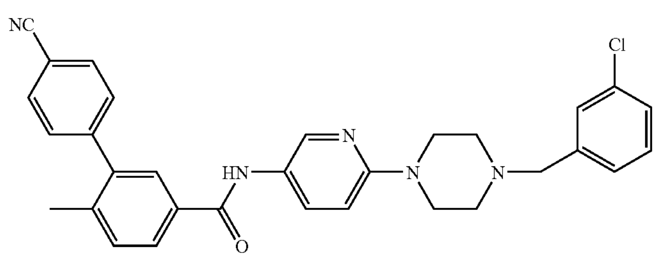 | LC-MS m/z 522.2 (M + 1) |
| 121 | 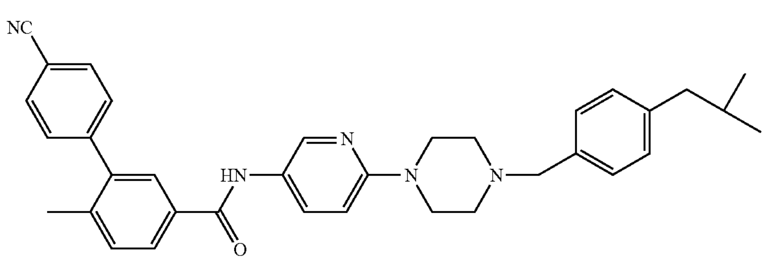 | LC-MS m/z 544.3 (M + 1) |

TABLE 1-continued
| Compound Number | Structure | Physical Data MS (m/z) |
|---|---|---|
| 122 | 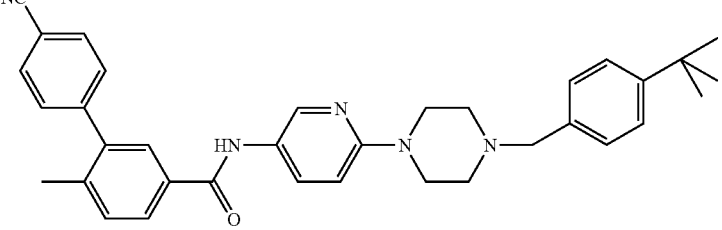 | LC-MS m/z 544.3 (M + 1) |
| 123 | 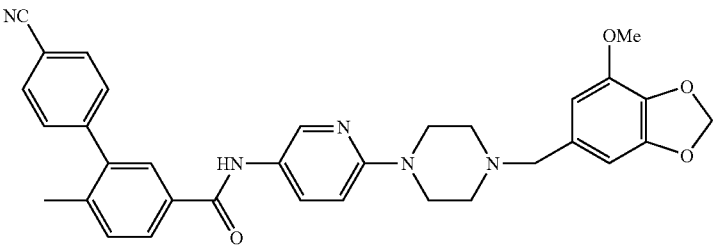 | LC-MS m/z 562.2 (M + 1) |
| 124 | 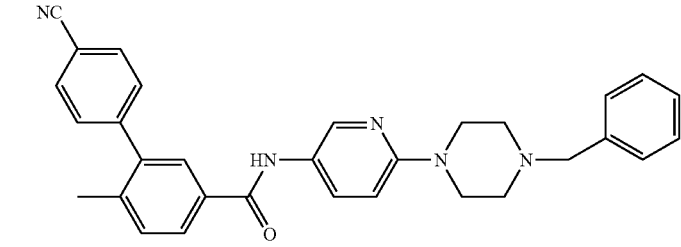 | LC-MS m/z 488.2 (M + 1) |
| 125 | 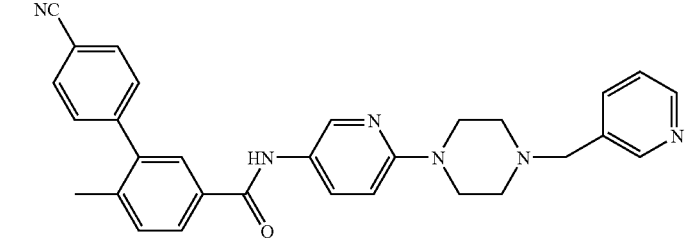 | LC-MS m/z 489.2 (M + 1) |
| 126 | 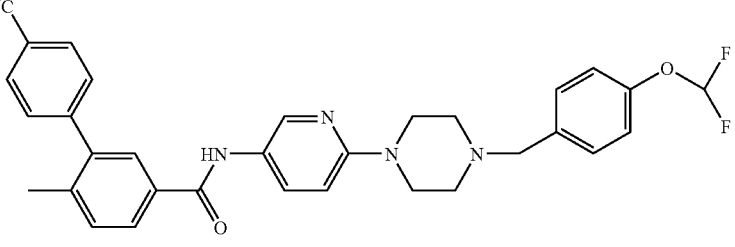 | LC-MS m/z 554.2 (M + 1) |
| 127 | 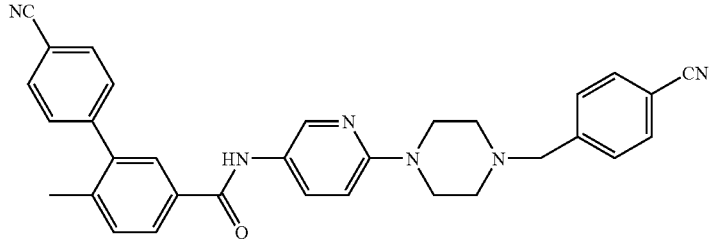 | LC-MS m/z 513.2 (M + 1) |

TABLE 1-continued

| Compound Number | Structure | Physical Data MS (m/z) |
|---|---|---|
| 128 | 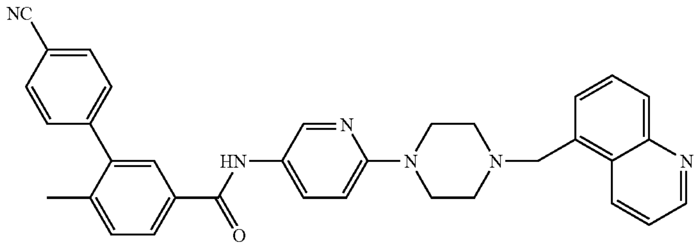 | LC-MS m/z 539.3 (M + 1) |
| 129 | 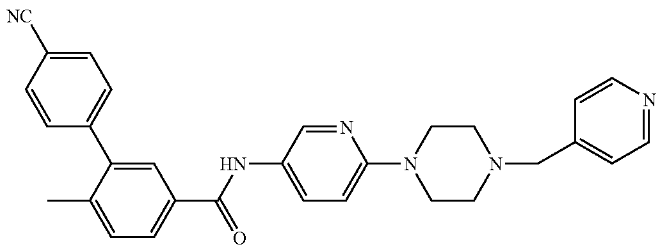 | LC-MS m/z 489.2 (M + 1) |
| 130 | 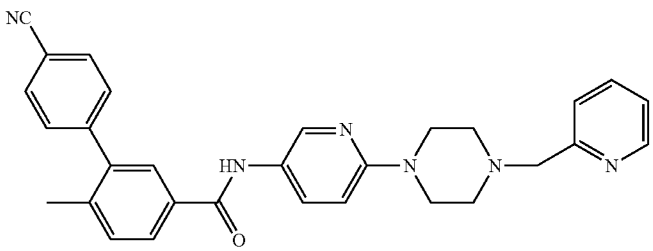 | LC-MS m/z 489.2 (M + 1) |
| 131 | 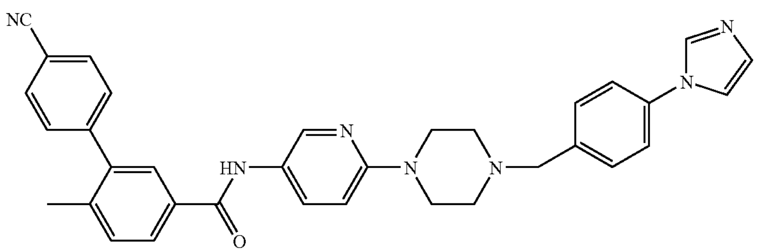 | LC-MS m/z 554.3 (M + 1) |
| 132 | 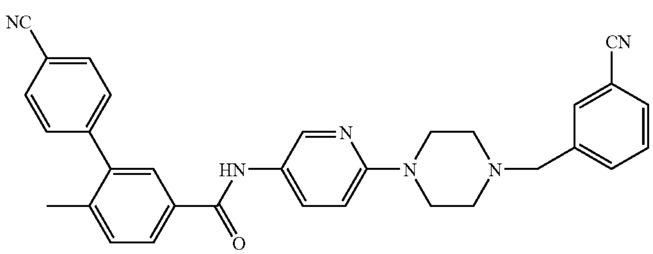 | LC-MS m/z 513.2 (M + 1) |
| 133 | 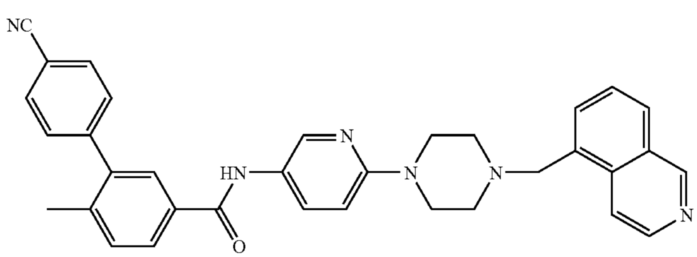 | LC-MS m/z 539.3 (M + 1) |

TABLE 1-continued

| Compound Number | Structure | Physical Data MS (m/z) |
|---|---|---|
| 134 | 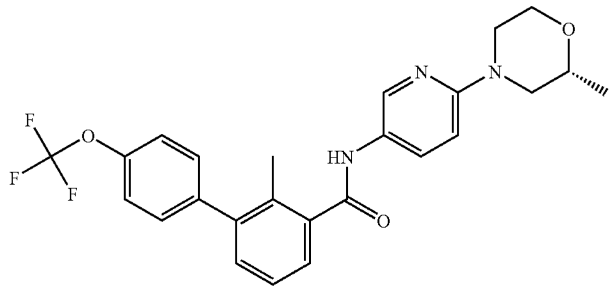 | LC-MS m/z 472.1 (M + 1) |
| 135 | 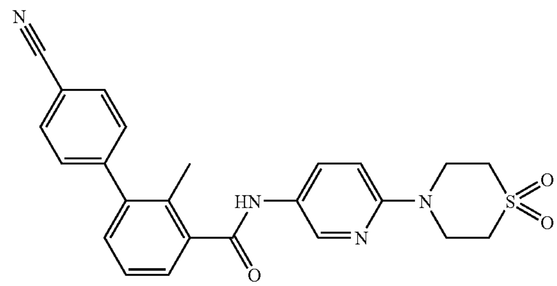 | LC-MS m/z 447.1 (M + 1) |
| 136 | 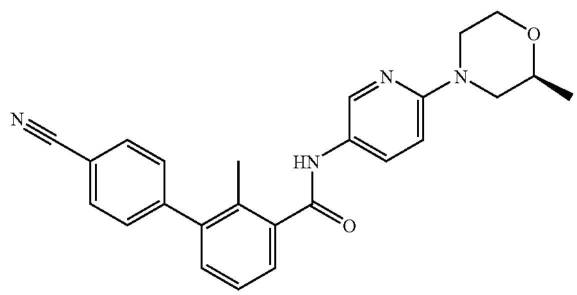 | LC-MS m/z 413.1 (M + 1) |
| 137 | 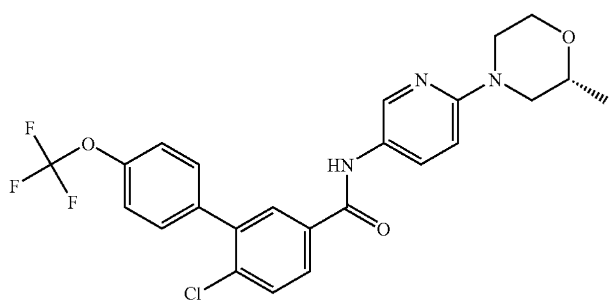 | LC-MS m/z 492.1 (M + 1) |
| 138 | 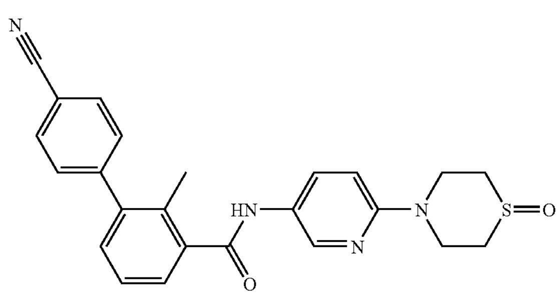 | LC-MS m/z 431.1 (M + 1) |

TABLE 1-continued

| Compound Number | Structure | Physical Data MS (m/z) |
|---|---|---|
| 139 | 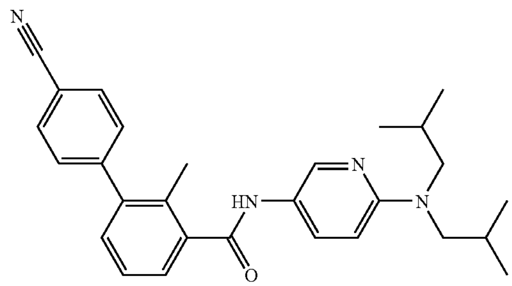 | LC-MS m/z 441.1 (M + 1) |
| 140 | 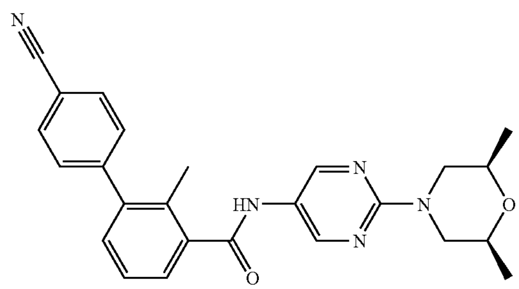 | LC-MS m/z 428.2 (M + 1) |
| 141 | 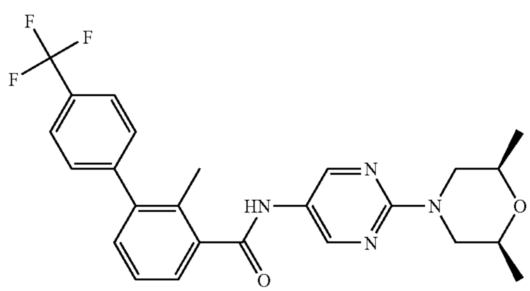 | LC-MS m/z 471.2 (M + 1) |
| 142 | 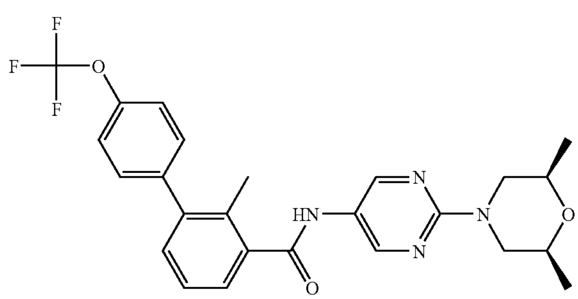 | LC-MS m/z 487.2 (M + 1) |
| 143 | 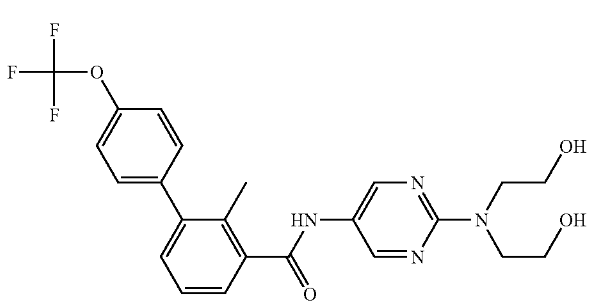 | LC-MS m/z 477.2 (M + 1) |

TABLE 1-continued
| Compound Number | Structure | Physical Data MS (m/z) |
|---|---|---|
| 144 | 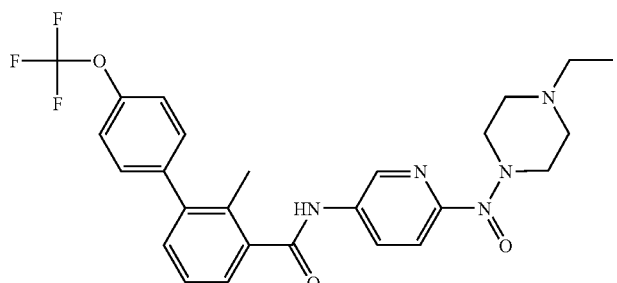 | LC-MS m/z 513.2 (M + 1) |
| 145 | 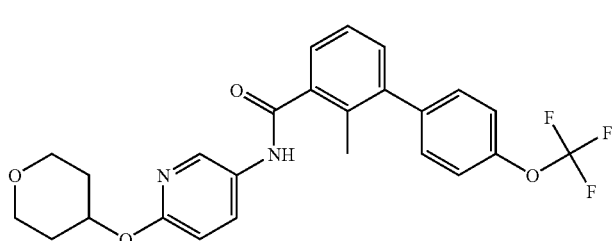 | LC-MS m/z 473.2 (M + 1) |
| 146 | 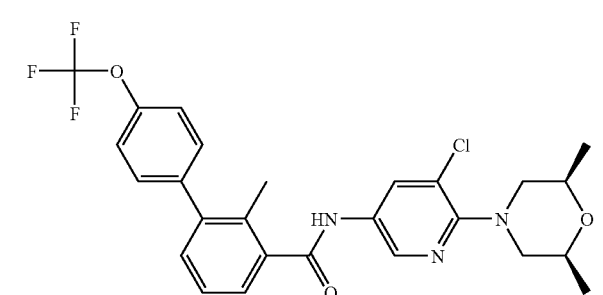 | LC-MS m/z 520.2 (M + 1) |
| 147 | 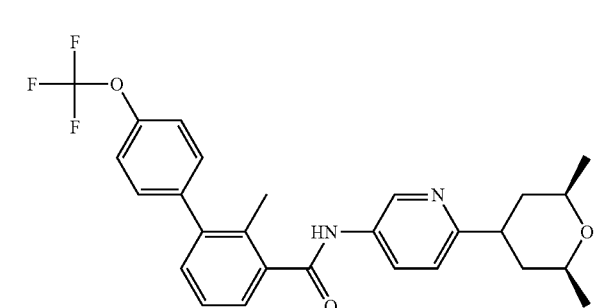 | LC-MS m/z 445.2 (M + 1) |
| 148 | 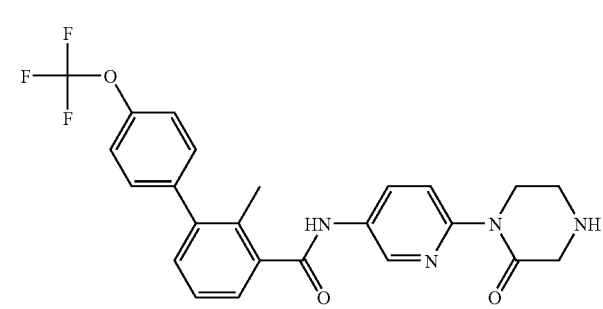 | LC-MS m/z 471.2 (M + 1) |

TABLE 1-continued

| Compound Number | Structure | Physical Data MS (m/z) |
| --- | --- | --- |
| 149 | 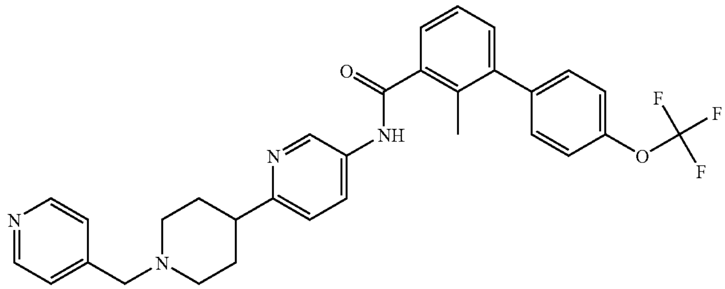 | LC-MS m/z 547.2 (M + 1) |
| 150 | 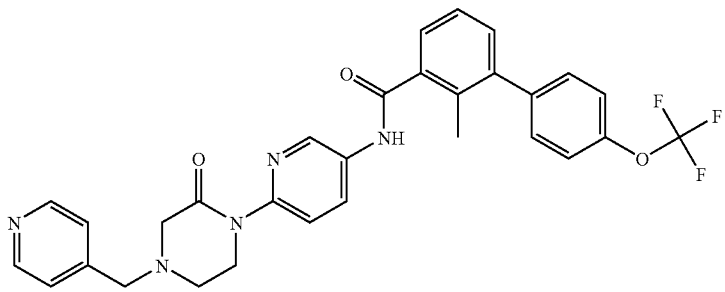 | LC-MS m/z 562.2 (M + 1) |
| 151 | 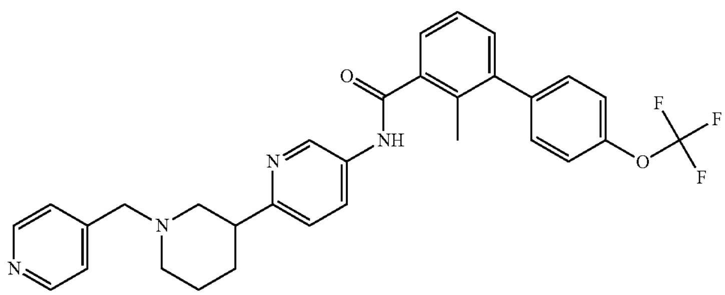 | LC-MS m/z 547.2 (M + 1) |
| 152 | 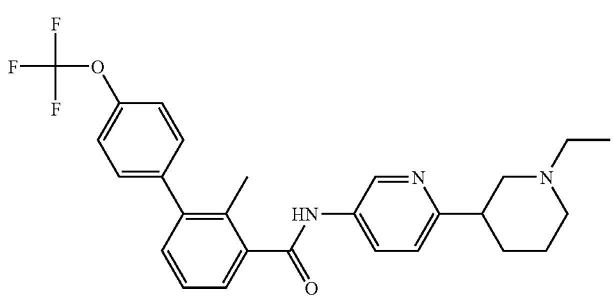 | LC-MS m/z 484.2 (M + 1) |
| 153 | 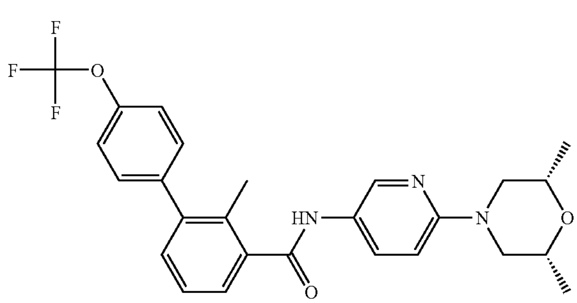 | LC-MS m/z 486.2 (M + 1) |

Compounds of the present invention are assayed to evaluate their capacity to inhibit the hedgehog signaling pathway.

Gli-Luc Reporter Assay for Hh Pathway Inhibition

Mouse TM3 cells (obtained from American Type Culture Collection, ATCC, Manassas, Va.) are cultured in DMEM/F12 medium (Gibco/Invitrogen, Carlsbad, Calif.) supplemented with 5% heat inactivated horse serum and 2.5% FBS (Gibco/Invitrogen, Carlsbad, Calif.), 50 unit/mL penicillin and 50 µg/mL of streptomycin (Gibco/Invitrogen, Carlsbad, Calif.) at 37° C. with 5% $CO_2$ in air atmosphere. TM3 cells were transfected with pTA-8xGli-Luc reporter plasmid. A stably transfected clone termed TMHh-12 was selected. TMHh-12 clone showed good response to Shh-N stimulation. To evaluate the IC50s of the antagonists, 8000 TMHh-12 cells were plated into each wells in 384-well plates with 50% DMEM/F12 medium supplemented with 2% FBS. After 12 hours, Hh pathway is activated by adding recombinant mouse Shh protein (expressed in *E. coli*, 8 µg/mL) or by adding Smo agonists. The testing compounds are added into plates with different concentrations. After 48 hours, the firefly luciferase luciferase activities are assayed with the Bright-Glo™ Luciferase Assay System (Promega, Madison, Wis.). The $IC_{50}$ is measured when the effect of the compound reduces the luminescence signal by 50%. Toxicity of these compounds are evaluated in TM3 cells using CellTiter Glo assays or by TM3-Luc cell line (a TM3 cell stably transfected with a constitutive luciferase expression vector).

Compounds of Formula I preferably have an $EC_{50}$ of less than 500 nM, more preferable less than 200 nM.

Cyto-Toxicity Assay

A cytotoxicity assay is performed to compare the effects of a compound of the invention on medulloblastoma cells (Daoy cells), basal cell carcinoma cells (TE354.T cells) and control cells (human normal fibroblast) according to the following procedure:

Daoy cells (medulloblastoma cell line) are purchased from ATCC, and cultured in Minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate and 10% FBS at 37° C. with 5% $CO_2$ in an air atmosphere.

TE354.T cells (from ATCC) are cultured in Dulbecco's modified Eagle's medium with 4 mM L-glutamine fetal bovine serum and 10% of FBS.

Normal human dermal fibroblast cells (Clonetics) are cultured in Fibroblast Growth Medium (Clonetics).

Each of the above cell lines are independently seeded into 96-well plates and cultured to a density of 5,000-10,000 cells/well. A compound of the invention, at different concentrations, is added into the cell cultures. After 2 days, the cell viability is evaluated with Cell Titer-Glo Luminescent Cell Viability Assay Kit (Promega) following the manufacturer's protocol. The cell viability is directly measured by luminescent signaling and $EC_{50}$s are measured when the signal is inhibited 50%.

Compounds of Formula I preferably have an $EC_{50}$ of less than 500 nM, more preferable less than 200 nM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

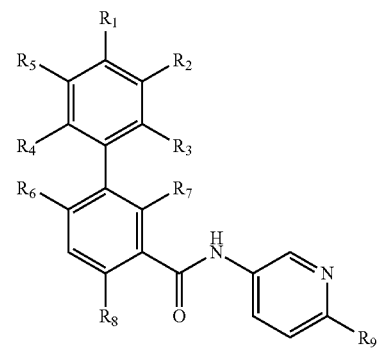

or a pharmaceutically acceptable salt or stereoisomer thereof, in which:

$R_1$ is selected from cyano, $C_{1-6}$alkyl, halosubstituted-$C_{1-6}$alkyl, $C_{1-6}$alkoxy, halosubstituted-$C_{1-6}$alkoxy, dimethyl-amino, $C_{1-6}$alkyl-sulfanyl and $C_{3-8}$heterocycloalkyl optionally substituted with up to two $C_{1-6}$alkyl radicals;

$R_2$ and $R_5$ are independently selected from hydrogen, cyano, halo, $C_{1-6}$alkyl, halosubstituted-$C_{1-6}$alkyl, $C_{1-6}$alkoxy, halosubstituted-$C_{1-6}$alkoxy and dimethylamino;

$R_3$ and $R_4$ are independently selected from hydrogen, halo, cyano, $C_{1-6}$alkyl, halosubstituted-$C_{1-6}$alkyl, $C_{1-6}$alkoxy and halosubstituted-$C_{1-6}$alkoxy;

$R_6$ and $R_7$ are independently selected from hydrogen, fluoro, chloro, bromo, $C_{1-6}$alkyl, halosubstituted-$C_{1-6}$alkyl, $C_{1-6}$alkoxy and halosubstituted-$C_{1-6}$alkoxy; with the proviso that $R_6$ and $R_7$ are not both hydrogen;

$R_8$ is selected from hydrogen, halo, $C_{1-6}$alkyl, halosubstituted-$C_{1-6}$alkyl, $C_{1-6}$alkoxy and halosubstituted-$C_{1-6}$alkoxy;

$R_9$ is selected from $-S(O)_2R_{11}$, $-OR_{11}$, $-C(O)R_{11}$, $-NR_{12a}R_{12b}$ and $-R_{11}$; wherein $R_{11}$ is selected from thiomorpholino, sulfonomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl and 1,4-diazepan-1-yl; $R_{12a}$ and $R_{12b}$ are independently selected from isobutyl, hydroxy-ethyl, wherein said thiomorpholino, sulfonomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl or 1,4-diazepan-1-yl of $R_9$ can be optionally substituted with 1 to 3 radicals independently selected from methyl, ethyl, methoxy, benzyl, thienyl-methyl, pyridinyl-methyl, benzo[d][1,3]dioxol-6-yl and 2,3-dihydrobenzo[b][1,4]dioxin-7-yl;

wherein said benzyl substituent of $R_9$ is optionally substituted with 1 to 3 radicals independently selected from methoxy, ethoxy, methyl-piperazinyl, methyl, trifluoromethoxy, chloro, fluoro and trifluoromethyl.

2. The compound of claim 1 in which:

$R_6$ and $R_7$ are independently selected from hydrogen methyl, chloro, fluoro, bromo, trifluoromethyl and methoxy; with the proviso that $R_6$ and $R_7$ are not both hydrogen; and $R_8$ is selected from hydrogen, fluoro, chloro, methyl and trifluoromethyl.

3. The compound of claim 2 in which:

$R_1$ is selected from cyano, methyl, ethyl, t-butyl, propyl, isobutyl, isopropyl, isopropyloxy, butoxy, methoxy, dimethyl-amino, ethoxy, methyl-sulfanyl, trifluoromethyl, trifluoromethoxy and piperazinyl optionally substituted with up to 2 methyl radicals;

$R_2$ and $R_5$ are independently selected from hydrogen, chloro, fluoro, cyano, methyl, trifluoromethyl, isopropyloxy, methoxy, ethoxy, trifluoromethoxy and dimethylamino; and $R_3$ and $R_4$ are independently selected from hydrogen, chloro, methyl, methoxy and cyano.

4. The compound of claim 3 in which $R_8$ is hydrogen.

5. A compound of claim 1 selected from the group consisting of:

N-(6-((2R,6S)-2,6-dimethylmorpholino)pyridin-3-yl)-2-methyl-4'-(trifluoromethoxy)-[1,1'-biphenyl]-3-carboxamide, 4'-cyano-6-methyl-biphenyl-3-carboxylic acid [6-(2,6-dimethyl-morpholin-4-yl)-pyridin-3-yl]-amide, 4'-Cyano-2-methyl-biphenyl-3-carboxylic acid (6-azepan-1-yl-pyridin-3-yl)-amide, 4'-Methoxy-2-methyl-biphenyl-3-carboxylic acid (6-azepan-1-yl-pyridin-3-yl)-amide, 4'-Methoxy-2-methyl-biphenyl-3-carboxylic acid [6-(2-methyl-morpholin-4-yl)-pyridin-3-yl]-amide, 6-Chloro-4'-dimethylamino-biphenyl-3-carboxylic acid (6-[1,4]oxazepan-4-yl-pyridin-3-yl)-amide, 6-Chloro-4'-dimethylamino-biphenyl-3-carboxylic acid (6-morpholin-4-yl-pyridin-3-yl)-amide, 6-Chloro-4'-dimethylamino-biphenyl-3-carboxylic acid (6-azepan-1-yl-pyridin-3-yl)-amide, 6-Chloro-4'-methoxy-biphenyl-3-carboxylic acid [6-(2-methyl-morpholin-4-yl)-pyridin-3-yl]-amide, 6-Chloro-4'-methoxy-biphenyl-3-carboxylic acid (6-[1,4]oxazepan-4-yl-pyridin-3-yl)-amide, 6-Chloro-4'-methoxy-biphenyl-3-carboxylic acid (6-azepan-1-yl-pyridin-3-yl)-amide, 6-Chloro-4'-methoxy-biphenyl-3-carboxylic acid (6-morpholin-4-yl-pyridin-3-yl)-amide, 4'-Methoxy-6-methyl-biphenyl-3-carboxylic acid (6-morpholin-4-yl-pyridin-3-yl)-amide, 4'-Methoxy-6-methyl-biphenyl-3-carboxylic acid (6-[1,4]oxazepan-4-yl-pyridin-3-yl)-amide, 4'-Methoxy-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid (6-[1,4]oxazepan-4-yl-pyridin-3-yl)-amide, 4'-Dimethylamino-6-methyl-biphenyl-3-carboxylic acid (6-morpholin-4-yl-pyridin-3-yl)-amide, 4'-Methoxy-6-methyl-biphenyl-3-carboxylic acid (6-azepan-1-yl-pyridin-3-yl)-amide, 4'-Ethoxy-6-methyl-biphenyl-3-carboxylic acid (6-azepan-1-yl-pyridin-3-yl)-amide, 6-Methyl-4'-methylsulfanyl-biphenyl-3-carboxylic acid (6-azepan-1-yl-pyridin-3-yl)-amide, 4'-Dimethylamino-6-methyl-biphenyl-3-carboxylic acid (6-azepan-1-yl-pyridin-3-yl)-amide, 3'-Chloro-6-methyl-4'-trifluoromethyl-biphenyl-3-carboxylic acid (6-azepan-1-yl-pyridin-3-yl)-amide, 6,4'-Dimethyl-biphenyl-3-carboxylic acid (6-azepan-1-yl-pyridin-3-yl)-amide, 4'-Ethyl-6-methyl-biphenyl-3-carboxylic acid (6-azepan-1-yl-pyridin-3-yl)-amide, 4'-tert-Butyl-6-methyl-biphenyl-3-carboxylic acid (6-azepan-1-yl-pyridin-3-yl)-amide, 6-Methyl-4'-propyl-biphenyl-3-carboxylic acid (6-azepan-1-yl-pyridin-3-yl)-amide, 4'-Isobutyl-6-methyl-biphenyl-3-carboxylic acid (6-azepan-1-yl-pyridin-3-yl)-amide, 4'-Isopropyl-6-methyl-biphenyl-3-carboxylic acid (6-azepan-1-yl-pyridin-3-yl)-amide, 6-Methyl-4'-trifluoromethyl-biphenyl-3-carboxylic acid (6-azepan-1-yl-pyridin-3-yl)-amide, 6-Methyl-4'-trifluoromethoxy-biphenyl-3-carboxylic acid (6-azepan-1-yl-pyridin-3-yl)-amide, 4'-Cyano-6-methyl-biphenyl-3-carboxylic acid (6-[1,4]oxazepan-4-yl-pyridin-3-yl)-amide, 4'-Cyano-6-methyl-biphenyl-3-carboxylic acid (6-azepan-1-yl-pyridin-3-yl)-amide, 4'-Cyano-6-methyl-biphenyl-3-carboxylic acid [6-(2-methyl-morpholin-4-yl)-pyridin-3-yl]-amide, 4'-Cyano-6-methyl-biphenyl-3-carboxylic acid (3,4,5,6-tetrahydro-2H-[1,2']bipyridinyl-5'-yl)-amide, 4'-Cyano-6-methyl-biphenyl-3-carboxylic acid (6-morpholin-4-yl-pyridin-3-yl)-amide, 4'-Cyano-6-methyl-biphenyl-3-carboxylic acid [6-(4-methyl-piperazin-1-yl)-pyridin-3-yl]-amide, 4'-Cyano-6-methoxy-biphenyl-3-carboxylic acid (6-azepan-1-yl-pyridin-3-yl)-amide, 4'-Cyano-2-methoxy-biphenyl-3-carboxylic acid (6-azepan-1-yl-pyridin-3-yl)-amide, 4'-Cyano-2-methyl-biphenyl-3-carboxylic acid (6-azepan-1-yl-pyridin-3-yl)-amide, 3'-Fluoro-4'-methoxy-6-methyl-biphenyl-3-carboxylic acid (6-azepan-1-yl-pyridin-3-yl)-amide, 4'-Isopropoxy-6-methyl-biphenyl-3-carboxylic acid (6-azepan-1-yl-pyridin-3-yl)-amide, 4'-Butoxy-6-methyl-biphenyl-3-carboxylic acid (6-azepan-1-yl-pyridin-3-yl)-amide, 3'-Chloro-4'-methoxy-6-methyl-biphenyl-3-carboxylic acid (6-azepan-1-yl-pyridin-3-yl)-amide, 4'-Methoxy-6,3'-dimethyl-biphenyl-3-carboxylic acid (6-azepan-1-yl-pyridin-3-yl)-amide, 4'-Cyano-6-methyl-biphenyl-3-carboxylic acid [6-(4-benzyl-[1,4]diazepan-1-yl)-pyridin-3-yl]-amide, 4'-Cyano-6-methyl-biphenyl-3-carboxylic acid [6-(4-thiophen-3-ylmethyl-[1,4]diazepan-1-yl)-pyridin-3-yl]-amide, 4'-Cyano-2-methyl-biphenyl-3-carboxylic acid [6-(2,6-dimethyl-morpholin-4-yl)-pyridin-3-yl]-amide, 4'-Methoxy-2-methyl-biphenyl-3-carboxylic acid [6-(2,6-dimethyl-morpholin-4-yl)-pyridin-3-yl]-amide, 2-Methyl-4'-trifluoromethyl-biphenyl-3-carboxylic acid [6-(2,6-dimethyl-morpholin-4-yl)-pyridin-3-yl]-amide, 2-Methyl-4'-trifluoromethoxy-biphenyl-3-carboxylic acid [6-(2,6-dimethyl-morpholin-4-yl)-pyridin-3-yl]-amide, 4'-Cyano-2-methyl-biphenyl-3-carboxylic acid [6-(2-methyl-morpholin-4-yl)-pyridin-3-yl]-amide, 4'-Cyano-6-methyl-biphenyl-3-carboxylic acid [6-(4-pyridin-4-ylmethyl-[1,4]diazepan-1-yl)-pyridin-3-yl]-amide, 4'-Cyano-6-methyl-biphenyl-3-carboxylic acid [6-(4-pyridin-3-ylmethyl-[1,4]diazepan-1-yl)-pyridin-3-yl]-amide, 4'-Cyano-6-methyl-biphenyl-3-carboxylic acid {6-[4-(2,6-dimethoxy-benzyl)-[1,4]diazepan-1-yl]-pyridin-3yl}-amide, 4'-Cyano-6-methyl-biphenyl-3-carboxylic acid {6-[4-(2-ethoxy-benzyl)-[1,4]diazepan-1-yl]-pyridin-3}-amide, 4'-Cyano-6-methyl-biphenyl-3-carboxylic acid (6-{4-[2-(4-methyl-piperazin-1-yl)-benzyl]-[1,4]diazepan-1-yl}-pyridin-3-yl)-amide, 4'-Cyano-6-methyl-biphenyl-3-carboxylic acid {6-[4-(4-methoxy-2,3-dimethyl-benzyl)-[1,4]diazepan-1-yl]-pyridin-3-yl}-amide, 4'-Cyano-6-methyl-biphenyl-3-carboxylic acid [6-(4-pyridin-2-ylmethyl-[1,4]diazepan-1-yl)-pyridin-3-yl]-amide,
4'-Cyano-6-methyl-biphenyl-3-carboxylic acid {6-[4-(2-trifluoromethoxy-benzyl)-[1,4]diazepan-1-yl]-pyridin-3-yl}-amide,
4'-Cyano-6-methyl-biphenyl-3-carboxylic acid {6-[4-(2-chloro-5-trifluoromethyl-benzyl)-[1,4]diazepan-1-yl]-pyridin-3-yl}-amide,
4'-Cyano-6-methyl-biphenyl-3-carboxylic acid {6-[4-(2,3-difluoro-benzyl)-[1,4]diazepan-1-yl]-pyridin-3-yl}-amide,
4'-Cyano-6-methyl-biphenyl-3-carboxylic acid {6-[4-(2-chloro-4-fluoro-benzyl)-[1,4]diazepan-1-yl]-pyridin-3-yl}-amide,
4'-Cyano-6-methyl-biphenyl-3-carboxylic acid {6-[4-(2,6-difluoro-benzyl)-[1,4]diazepan-1-yl]-pyridin-3-yl}-amide,
4'-Cyano-6-trifluoromethyl-biphenyl-3-carboxylic acid [6-(2,6-dimethyl-morpholin-4-yl)-pyridin-3-yl]-amide,
2-Chloro-4'-cyano-biphenyl-3-carboxylic acid [6-(2,6-dimethyl-morpholin-4-yl)-pyridin-3-yl]-amide,
4'-Cyano-6-ethyl-biphenyl-3-carboxylic acid [6-(2,6-dimethyl-morpholin-4-yl)-pyridin-3-yl]-amide,
4'-Cyano-6-methyl-biphenyl-3-carboxylic acid {6-[4-(3-fluoro-benzyl)-piperazin-1-yl]-pyridin-3-yl}-amide,
4'-Cyano-6-methyl-biphenyl-3-carboxylic acid {6-[4-(2-trifluoromethoxy-benzyl)-piperazin-1-yl]-pyridin-3-yl}-amide,
4'-Cyano-6-methyl-biphenyl-3-carboxylic acid {6-[4-(3-chloro-benzyl)-piperazin-1-yl]-pyridin-3-yl}-amide,
4'-Cyano-6-methyl-biphenyl-3-carboxylic acid [6-(4-benzyl-piperazin-1-yl)-pyridin-3-yl]-amide,
4'-Cyano-6-methyl-biphenyl-3-carboxylic acid [6-(4-pyridin-3-ylmethyl-piperazin-1-yl)-pyridin-3-yl]-amide,
4'-Cyano-6-methyl-biphenyl-3-carboxylic acid [6-(4-pyridin-4-ylmethyl-piperazin-1-yl)-pyridin-3-yl]-amide,
4'-Cyano-6-methyl-biphenyl-3-carboxylic acid [6-(4-pyridin-2-ylmethyl-piperazin-1-yl)-pyridin-3-yl]-amide,
(R)-2-methyl-N-(6-(2-methylmorpholino)pyridin-3-yl)-4'-(trifluoromethoxy)biphenyl-3-carboxamide,
4'-cyano-2-methyl-N-(6-sulfonylmorpholinopyridin-3-yl) biphenyl-3-carboxamide,
(S)-4'-cyano-2-methyl-N-(6-(2-methylmorpholino)pyridin-3-yl)biphenyl-3-carboxamide,
(R)-6-chloro-N-(6-(2-methylmorpholino)pyridin-3-yl)-4'-(trifluoromethoxy)biphenyl-3-carboxamide,
2-methyl-N-(6-(tetrahydro-2H-pyran-4-yloxy)pyridin-3-yl)-4'-(trifluoromethoxy)biphenyl-3-carboxamide,
N-(6-(4-ethylpiperazine-1-carbonyl)pyridin-3-yl)-2-methyl-4'-(trifluoromethoxy)biphenyl-3-carboxamide,
2-methyl-N-(6-(2-oxopiperazin-1-yl)pyridin-3-yl)-4'-(trifluoromethoxy)biphenyl-3-carboxamide,
2-methyl-N-(6-(2-oxo-4-(pyridin-4-ylmethyl)piperazin-1-yl)pyridin-3-yl)-4'-(trifluoromethoxy)biphenyl-3-carboxamide;
2-methyl-N-(6-(1-(pyridin-4-ylmethyl)piperidin-3-yl)pyridin-3-yl)-4'-(trifluoromethoxy)biphenyl-3-carboxamide, and
N-(6-(1-ethylpiperidin-3-yl)pyridin-3-yl)-2-methyl-4'-(trifluoromethoxy)biphenyl-3-carboxamide,
or a pharmaceutically acceptable salt or stereoisomer thereof.

6. A method of inhibiting the hedgehog pathway in a cell, comprising contacting the cell with a compound of claim 1.

7. The method of claim 6 wherein the cell has a phenotype of Ptc loss-of-function, hedgehog gain-of-function, smoothened gain-of-function or Gli gain-of-function.

8. The method of claim 6, wherein the compound is administered to an animal as part of a therapeutic application, wherein the therapeutic application is selected from pancreatic cancer, prostate cancer, medulloblastoma, basal cell carcinoma, and small-cell lung cancer.

9. A method for inhibiting unwanted proliferation of a cell, comprising contacting the cell with a compound of claim 1, wherein the cell is selected from pancreatic cancer, prostrate cancer, medulloblastoma, basal cell carcinoma and small-cell lung cancer.

10. A compound, N-(6-((2R,6S)-2,6-dimethylmorpholino)pyridin-3-yl)-2-methyl-4'-(trifluoromethoxy)[1,1'-biphenyl]-3-carboxamide, of the formula:

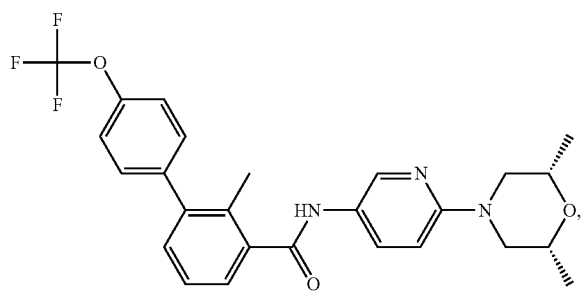

or a pharmaceutically acceptable salt thereof.

11. A compound, N-(6((2R,6S)-2,6-dimethylmorpholino)pyridin-3-yl)-2-methyl-4'-(trifluoromethoxy)-[1,1'-biphenyl]-3-carboxamide, of the formula:

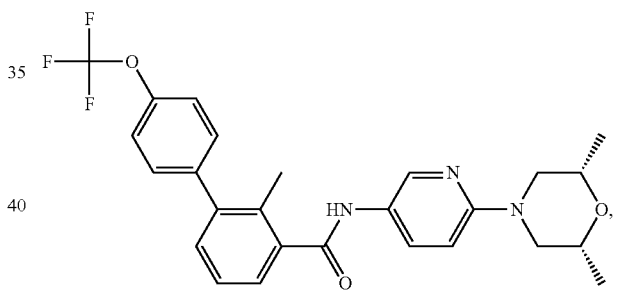

or a pharmaceutically acceptable salt or stereoisomer thereof.

12. A compound, N-(6((2R,6S)-2,6-dimethylmorpholino)pyridin-3-yl)-2-methyl-4'-(trifluoromethoxy)-[1,1'-biphenyl]-3-carboxamide, of the formula:

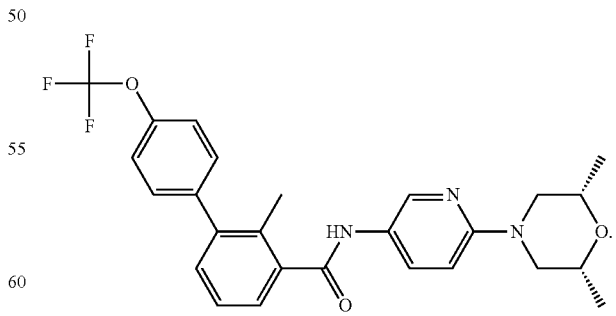

* * * * *

UNITED STATES PATENT AND TRADEMARK OFFICE

(12)        CERTIFICATE EXTENDING PATENT TERM
UNDER 35 U.S.C. § 156

| | | | |
|---|---|---|---|
| (68) | PATENT NO. | : | 8,178,563 |
| (45) | ISSUED | : | May 15, 2012 |
| (75) | INVENTOR | : | Wenqi Gao et al. |
| (73) | PATENT OWNER | : | Sun Pharma Global FZE |
| (95) | PRODUCT | : | ODOMZO® (sonidegib phosphate) |

This is to certify that an application under 35 U.S.C. § 156 has been filed in the United States Patent and Trademark Office, requesting extension of the term of U.S. Patent No. 8,178,563 based upon the regulatory review of the product ODOMZO® (sonidegib phosphate) by the Food and Drug Administration. According to United States Patent and Trademark Office records, the original expiration date of the patent as of the date of issuance of this certificate is February 6, 2029. Because it appears that the requirements of the law have been met, this certificate extends the term of the patent for the period of

(94)                              168 days subject to the payment of maintenance fees as provided by law, with all rights pertaining thereto as provided by 35 U.S.C. § 156.

I have caused the seal of the United States Patent and Trademark Office to be affixed this 23rd day of October 2020.

Andrei Iancu
Under Secretary of Commerce for Intellectual Property and
   Director of the United States Patent and Trademark Office